United States Patent
Gonzalez et al.

(10) Patent No.: US 9,416,364 B2
(45) Date of Patent: Aug. 16, 2016

(54) REVERSE BETA OXIDATION PATHWAY

(75) Inventors: Ramon Gonzalez, Houston, TX (US);
James Clomburg, Houston, TX (US);
Clementina Dellomonaco, Wilmington, DE (US); Elliot N. Miller, Houston, TX (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 13/983,885

(22) PCT Filed: Feb. 7, 2012

(86) PCT No.: PCT/US2012/024051
§ 371 (c)(1),
(2), (4) Date: Aug. 6, 2013

(87) PCT Pub. No.: WO2012/109176
PCT Pub. Date: Aug. 16, 2012

(65) Prior Publication Data
US 2013/0316413 A1    Nov. 28, 2013

Related U.S. Application Data

(60) Provisional application No. 61/440,192, filed on Feb. 7, 2011.

(51) Int. Cl.
| | | |
|---|---|---|
| *C12N 15/70* | (2006.01) | |
| *C12P 5/02* | (2006.01) | |
| *C12P 7/40* | (2006.01) | |
| *C12P 7/04* | (2006.01) | |
| *C12P 7/16* | (2006.01) | |
| *C12P 7/42* | (2006.01) | |
| *C12P 7/64* | (2006.01) | |

(52) U.S. Cl.
CPC . *C12N 15/70* (2013.01); *C12P 5/02* (2013.01); *C12P 5/026* (2013.01); *C12P 7/04* (2013.01); *C12P 7/16* (2013.01); *C12P 7/40* (2013.01); *C12P 7/42* (2013.01); *C12P 7/6409* (2013.01); *C12Y 102/0105* (2013.01); *Y02E 50/10* (2013.01); *Y02P 20/52* (2015.11)

(58) Field of Classification Search
None
See application file for complete search history.

(56) References Cited

FOREIGN PATENT DOCUMENTS

| EP | 12829682.9 | 7/2014 |
|---|---|---|
| WO | WO2009111672 | 9/2009 |
| WO | WO2012109176 | 8/2012 |

OTHER PUBLICATIONS

Kizer L et al. Applicatoin of Functional Genomics to Pathway Optimization for Increases Isoprenoid Production. 2008. Applied and Environmental Microbiology. vol. 74, No. 10. p. 3229-3241.*

Prather KLJ et al. De novo biosynthetic pathways: a rational design of microbial chemical factories. 2008. Current Opinion in Biotechnology. 19:468-474.*

Atsumi, S. et al. Metabolic engineering of *Escherichia coli* for 1-butanol production. Metab. Eng. 10, 305-311 (2008).

Atsumi, S., et al. Non-fermentative pathways for synthesis of branchedchain higher alcohols as biofuels. Nature 451, 86-89 (2008).

Bond-Watts, B.B., et al., Enzyme mechanism as a kinetic control element for designing synthetic biofuel pathways. Nat. Chem. Biol. 7, 222-227 (2011).

Clark, D.P. & Cronan, J. E. in *Escherichia coli* and *Salmonella*: cellular and molecular biology (ed. Neidhart, F.C.) Ch. 3.4.4, 343-357 (American Society for Microbiology, Washington DC, 2005).

Cronan, J. E. & Thomas, J. Bacterial fatty acid synthesis and its relationships with polyketide synthetic pathways. Methods Enzymol. 459, 395-433 (2009).

Dellomonaco, C., Rivera, C., Campbell, P. & Gonzalez, R. Engineered respiro-fermentative metabolism for the production of biofuels and biochemicals from fatty acid-rich feedstocks. Appl. Environ. Microbiol. 76, 5067-5078 (2010).

Dellomonaco, C., Clomburg, J.M., Miller, E.N., and Gonzalez, R. Engineered reversal of the β-oxidation cycle for the synthesis of fuels and chemicals. Nature 476, 355-359 (2011).

Eppler, T. & Boos, W. Glycerol-3-phosphate-mediated repression of malT in *Escherichia coli* does not require metabolism, depends on enzyme IIA(Glc) and is mediated by cAMP levels. Mol. Microbiol. 33, 1221-1231 (1999).

Frias, et al., Purification and characterization of OleA from Xanthomonas campestris and demonstration of a nondecarboxylative Claisen condensation reaction. Journal of Biological Chemistry, 286:10930-10938 (2011).

Haapalainen, A.M., et al., The thiolase superfamily: condensing enzymes with diverse reaction specificities. Trends Biochem. Sci. 31, 64-71 (2006).

Handke, P., et al., Application and engineering of fatty acid biosynthesis in *Escherichia coli* for advanced fuels and chemicals. Metab. Eng. 13, 28-3 (2010).

Hoffmeister, M., et al., Mitochondrial trans-2-Enoyl-CoA Reductase of Wax Ester Fermentation from Euglena gracilis Defines a New Family of Enzymes Involved in Lipid Synthesis. Journal of Biological Chemistry, 280, 4329-4338 (2005).

(Continued)

*Primary Examiner* — Paul Holland
(74) *Attorney, Agent, or Firm* — Boulware & Valoir

(57) ABSTRACT

The invention relates to recombinant microorganisms that have been engineered to produce various chemicals using genes that have been repurposed to create a reverse beta oxidation pathway. Generally speaking, the beta oxidation cycle is expressed and driven in reverse by modifying various regulation points for as many cycles as needed, and then the CoA thioester intermediates are converted to useful products by the action of termination enzymes.

7 Claims, 12 Drawing Sheets

(56) References Cited

OTHER PUBLICATIONS

Ishige T., et al., Wax Ester Production from n-Alkanes by *acinetobacter* sp. Strain M-1: Ultrastructure of Cellular Inclusions and Role of Acyl Coenzyme A Reductase. Applied and Environmental Microbiology, 68, 1192-1195 (2002).

Kim, Y., et al., Construction of an *Escherichia coli* K-12 mutant for homoethanologenic fermentation of glucose or xylose without foreign genes. Applied and Environmental Microbiology, 73, 1766-1771 (2007).

Lalman, J.A. & Bagley, D.M. Extracting long-chain fatty acids from a fermentation medium. J. Am. Oil Chem. Soc. 81, 105-110 (2004).

Lennen, R.M., et al., A process for microbial hydrocarbon synthesis: Overproduction of fatty acids in *Escherichia coli* and catalytic conversion to alkanes. Biotechnol. Bioeng. 106, 193-202 (2010).

Neidhart, F.C., et al., Culture media for enterobacteria. Journal of Bacteriology 119, 736-747 (1974).

Poirier, Y., et al., Peroxisomal β-oxidation—A metabolic pathway with multiple functions. Biochim. Biophys. Acta 1763, 1413-1426 (2006).

Reiser, S. and Somerville, C. Isolation of mutants of Acinetobacter calcoaceticus deficient in wax ester synthesis and complementation of one mutation with a gene encoding a fatty acyl coenzyme a reductase. J. of Bacteriol., 179, 2969-2975 (1997).

Rotte, C., et al., Pyruvate:NADP+ oxidoreductase from the mitochondrion of Euglena gracilis and from the apicomplexan Cryptosporidium parvum: a biochemical relic linking pyruvate metabolism in mitochondriate and amitochondriate protists. Molecular Biology and Evolution, 18, 710-720 (2001).

Schirmer, A., et al., Microbial Biosynthesis of Alkanes. Science, 329, 559-562 (2010).

Schutte, H., et al., Purification and Properties of Formaldehyde Dehydrogenase and Formate Dehydrogenase from Candida boidinii. European Journal of Biochemistry, 62, 151-160 (1976).

Shen, C.R. & Liao, J.C. Metabolic engineering of *Escherichia coli* for 1-butanol and 1-propanol production via the keto-acid pathways. Metab. Eng. 10, 312-320 (2008).

Steen, E.J. et al. Microbial production of fatty-acid-derived fuels and chemicals from plant biomass. Nature 463, 559-562 (2010).

Sukovich, D.J., et al., Structure, function, and insights into the biosynthesis of a head-to-head hydrocarbon in Shewanella oneidensis strain MR-1. Applied and Environmental Microbiology, 76, 3842-3849 (2010a).

Sukovich, D.J., et al., Widespread head-to-head hydrocarbon biosynthesis in bacteria and role of OleA. Applied and Environmental Microbiology, 76, 3850-3862 (2010b).

Yazdani, S.S. & Gonzalez, R. Engineering *Escherichia coli* for the efficient conversion of glycerol to ethanol and co-products. Metab. Eng. 10, 340-351 (2008).

Andrey Yu Gulevich et al: "Metabolic engineering of for 1-butanol biosynthesis through the inverted aerobic fatty acid beta-oxidation pathway", Biotechnology Letters, Springer Netherlands, Dordrecht, vol. 34, No. 3, Nov. 22, 2011, pp. 463-469.

Yan-Ning Zheng et al: "Optimization of 1-18 fatty alcohol biosynthesis pathway for selectively enhanced production of C12/14 and C16/18 fatty alcohols in engineered *Escherichia coli*", Microbial Cell Factories, Biomed Central, London, NL, vol. 11, No. 1, May 20, 2012, p. 65.

\* cited by examiner

Fig. 4 Proposed metabolic platform for the efficient synthesis of hydrocarbons. Reactions ①~④ are as indicated in Fig. 2. Reaction ⑤ indicates the synthesis of alkanes from acyl-CoAs as shown in Fig. 1a. Reaction ⑥ indicates the synthesis of alkenes from acyl-CoAs via the head-to-head condensation mechanism shown in Fig. 1b. 2[H]=NAD(P)H=FADH$_2$= Fd$_{red}$.

REVERSE BETA OXIDATION PATHWAY

PRIOR RELATED APPLICATIONS

This application is a National Phase filing under 35 U.S.C. §371 of International Application PCT/US2012/024051 filed on Feb. 7, 2012 which claims priority to 61/440,192, filed Feb. 7, 2011, Both applications are expressly incorporated herein by reference in their entirety.

FEDERALLY SPONSORED RESEARCH STATEMENT

This invention was made with government support under CBET-1134541 and CBET-1067565 awarded by the National Science Foundation. The government has certain rights in the invention.

FIELD OF THE INVENTION

The invention relates to recombinant microorganisms that have been engineered to produce alcohols carboxylic acids, alkanes or alkenes, using genes that have been repurposed to create a reverse beta oxidation pathway.

Generally speaking, the beta oxidation cycle is driven in reverse for as many cycles as needed, and then the CoA thioester intermediates can then be converted to useful products by the action of different types of termination enzymes: i) thioesterases, or acyl-CoA:acetyl-CoA transferases, or phosphotransacylases and carboxylate kinases (which form carboxylic acids) or ii) alcohol-forming coenzyme-A thioester reductases (which make alcohols) or iii) aldehyde-forming CoA thioester reductases and alcohol dehydrogenases (which together form alcohols) or iv) aldehyde-forming CoA thioester reductases and aldehyde decarbonylases (which together form alkanes or terminal alkenes) or v) olefin-forming enzymes (such as OleA, OleB, OleC, OleD, which together form internal alkenes or terminal alkenes or trienes or alkenols).

The carboxylic acids include monocarboxylic acids, β-keto acids, β-hydroxy acids, and trans-$\Delta^2$-fatty acids of different chain lengths. The alcohols include n-alcohols, β-keto alcohols, 1,3-diols, and trans-$\Delta^2$-alcohols of different chain lengths. Alkanes include aliphatic alkanes of different chain lengths. Aliphatic alkenes (also called olefins) include terminal olefins, internal olefins, trienes, and alkenols.

BACKGROUND OF THE INVENTION

In recent years much effort has been devoted to the biological production of renewable fuels such as ethanol. However, ethanol is not an ideal fuel, suffering from problems such as high hygroscopicity, high vapor pressure and low energy density. These qualities make ethanol incompatible with the current facilities used in the storage, distribution and use of liquid transportation fuels.

Higher-chain (C≥4) alcohols (e.g. n-butanol), fatty acid methyl esters (FAMEs) and hydrocarbons (alkanes and alkenes) offer several advantages compared to ethanol, including reduced hygroscopicity, reduced volatility, and higher energy density. These qualities make n-butanol and other higher alcohols more compatible with our current infrastructure for storage, distribution and usage.

The aforementioned long-chain fuels and chemicals are generated from short-chain metabolic intermediates through pathways that require carbon-chain elongation. However, biological efforts to date have been less than satisfactory, particularly where non-native genes are introduced to drive synthesic of longer chain molecules.

Therefore, what is needed in the art are better biological methods of making higher-chain (C≥4) fuels (e.g. alcohols, fatty acid methyl esters, FAMEs, and hydrocarbons) that are more efficient and cost effective than are currently available. The ideal method would also allow the production of chemicals, such as carboxylic acids and alcohols, that can be used as feedstocks in other industries.

SUMMARY OF THE INVENTION

We have developed an alternative approach to engineering microbes to make chemicals, such as alcohols, carboxylic acids, alkanes, and alkenes, that uses a functional reversal of the β-oxidation cycle as a metabolic platform for the synthesis of alcohols and carboxylic acids with various chain lengths and functionalities (FIG. 1A).

This pathway operates with coenzyme-A (CoA) thioester intermediates and directly uses acetyl-CoA for acyl-chain elongation (rather than first requiring ATP-dependent activation to malonyl-CoA), characteristics that enable product synthesis at maximum carbon and energy efficiency. The reversal of the β-oxidation cycle was engineered in *Escherichia coli* and used in combination with endogenous dehydrogenases and thioesterases to synthesize n-alcohols, fatty acids and 3-hydroxy-, 3-keto- and trans-$\Delta$2-carboxylic acids.

The superior nature of the engineered pathway was demonstrated by producing higher-chain linear n-alcohols (C≥4) and extracellular long-chain fatty acids (C>10) at higher efficiency than previously reported. The ubiquitous nature of β-oxidation, aldehyde/alcohol dehydrogenase, thioesterase, decarbonylase enzymes has the potential to enable the efficient synthesis of these products in other industrial organisms such as *S. cerevisiae, Z. mobilis, B. subtilis*, etc.

Although we have exemplified n-butanol, 4-C 3-hydroxy-, 3-keto- and trans-$\Delta$2-carboxylic acids, longer-chain (C>4) n-alcohols, and long-chain (C>10) fatty acids herein, we have also shown that with judicious use of starting materials and enzymes, we can also make other carboxylic acids, alcohols, alkanes and alkenes, depending on which termination enzymes are overexpressed in the engineered microorganism.

We have already engineered a one-turn reversal of the beta-oxidation cycle for the production of n-butanol in *E. coli*, an organism considered unable to produce this alcohol in the absence of foreign genes. This approach, called herein an "endogenous" or "native" gene approach, is not based on transferring pathways from organisms that naturally produce n-butanol, but native genes and proteins are repurposed to produce butanol by manipulation of pathways.

In general, our methodology to drive the reversed β-oxidation cycle involves the following three steps: 1) functionally expressing the beta oxidation cycle in the absence of its naturally inducing substrates (i.e. absence of fatty acids) and presence of a non-fatty acid carbon source (e.g. presence of glucose); 2) driving the beta oxidation cycle in the reverse/biosynthetic direction (as opposed to its natural catabolic/degradative direction); and 3) expressing termination enzymes that act on the appropriate intermediate of the beta oxidation cycle to make desired products.

In more detail, the recombinant engineering is:

1) Express the β-Oxidation Cycle in the Absence of its Naturally Inducing Substrates (i.e. Absence of Fatty Acids) and Presence of a Non-Fatty Acid Carbon Source (e.g. Presence of Glucose):

In order to express the β-oxidation cycle, first i) mutations fadR and atoC(c) enable expression of the genes encoding beta oxidation enzymes in the absence of fatty acids; ii) an arcA knockout (ΔarcA) enables the expression of genes encoding beta oxidation cycle enzymes/proteins under anaerobic/microaerobic conditions (microaerobic/anaerobic conditions are used in the production of fuels and chemicals but lead to repression of beta oxidation genes by ArcA); and iii) replacement of native cyclic AMP receptor protein (crp) with a cAMP-independent mutant (crp*) enables the expression of genes encoding beta oxidation cycle enzymes/proteins in the presence of a catabolite-repressing carbon source such as glucose (glucose is the most widely used carbon source in fermentation processes and represses the beta oxidation genes).

2) Driving the Beta Oxidation Cycle in the Reverse/Biosynthetic Direction (as Opposed to its Natural Catabolic/Degradative Direction).

In addition to functionally expressing the β-oxidation cycle, we propose the following modifications to achieve the reverse operation of this pathway: iv) the use of microaerobic/anaerobic conditions prevents/minimizes the metabolism of acetyl-CoA through the tricarboxylic acids (TCA) cycle and makes acetyl-CoA available to drive the beta oxidation cycle in the reverse/biosynthetic direction; v) pta (or ackA or both), poxB, adhE, yqhD, and eutE knockouts block/reduce the synthesis of acetate (Δpta or ΔackA and poxB) and ethanol (ΔadhE, ΔyqhD, and ΔeutE) from acetyl-CoA and therefore make acetyl-CoA available to drive the beta oxidation cycle in the reverse/biosynthetic direction; vi) overexpression of thiolases, the first step in the reversal of the beta oxidation cycle, enable the channeling of acetyl-CoA into this pathway and hence its operation in the reverse direction; vii) ldhA, mgsA, and frdA knockouts block/reduce the synthesis of lactate (ΔldhA and ΔmgsA) and succinate (ΔfrdA) from pyruvate and phosphoenolpyruvate, respectively, making more phosphoenolpyruvate and pyruvate available for the synthesis acetyl-CoA and therefore making acetyl-CoA available to drive the beta oxidation cycle in the reverse/biosynthetic direction; viii) overexpression of pyruvate:flavodoxin oxidoreductase (ydbK) and acyl-CoA dehydrogenase (ydiO and ydiQRST) enables the coupling of pyruvate oxidation (pyruvate→acetyl-CoA+$CO_2$+$Fd_{red}$) and trans-$\Delta^2$-enoyl-CoA reduction (trans-$\Delta^2$-enoyl-CoA+$Fd_{red}$→acyl-CoA) and hence drive the beta oxidation in the reverse direction.

3) Conversion of CoA Thioester Intermediates to the Desired End Products.

Generally speaking, there are several termination enzymes that will pull reaction intermediates out the reverse β-oxidation cycle and produce the desired end product (FIG. 1A):

i) CoA thioester hydrolases/thioesterases, or acyl-CoA: acetyl-CoA transferases, or phosphotransacylases and carboxylate kinases for carboxylic acids (i.e. short, medium, and long-chain monocarboxylic acids, β-keto acids, β-hydroxy acids, trans-$\Delta^2$-fatty acids), ii) alcohol-forming CoA thioester reductases for alcohols (i.e. short, medium, and long-chain n-alcohols, β-keto alcohols, 1,3-diols, trans-$\Delta^2$-alcohols), iii) aldehyde-forming CoA thioester reductases and alcohol dehydrogenases which together form alcohols (i.e. short, medium, and long-chain n-alcohols, β-keto alcohols, 1,3-diols, trans-$\Delta^2$-alcohols). One or more of these termination enzymes can be overexpressed, as needed depending on the desired end product.

iv) aldehyde-forming CoA thioester reductases and aldehyde decarbonylases (which together form alkanes or terminal alkenes of different chain lengths), and v) olefin-forming enzymes (which together form aliphatic internal alkenes or terminal alkenes or trienes or alkenols).

The termination enzymes can be native or non-native as desired for particular products, but it is preferred that the reverse beta oxidation cycle use native genes.

4. Regulation of Product Chain Length.

The chain length of thioester intermediates determines the length of end products, and can be controlled by using appropriate termination enzymes with the desired chain-length specificity. Additionally, chain elongation can be inhibited or promoted by reducing or increasing the activity of thiolases with the desired chain-length specificity. These two methods can be used together or independently. For example:

i) knockout of fadA, fadI, and paaJ to avoid chain elongation beyond 1-to-2 turns of the cycle (generates 4- & 6-carbon intermediates and products, or 5- & 7-carbon intermediates and products, depending on the use of acetyl-CoA or propionyl-CoA as primer/starter molecule) and overexpression of the short-chain thiolases yqeF or atoB or short chains alcohol dehydrogenases such as fucO or yqhD;

ii) overexpression of fadB, fadI, and paaJ to promote chain elongation and overexpression of long-chain thiolases tesA, tesB, fadM, ybgC or yciA or long chain alcohol dehydrogenases such as ucpA, ybbO, yiaY, betA, ybdH or eutG; The term "appropriate" is used herein to refer to an enzyme with the required specificity toward a given intermediate (i.e. acyl-CoA, enoyl-CoA, hydroxyacyl-CoA, and ketoacyl-CoA) of a specific chain length. Please note that the chain length of the thioester intermediates can be controlled by manipulating thiolases (as described above), and hence only thioesters of the desired chain length will be available to the termination enzymes.

| Abbreviation | Definition |
|---|---|
| Δ | Refers to reduced activity wherein reduced activity is at least an 75% reduction of wild type activity, and preferably, 80, 85, 90, 95 or 100% reduction. 100% reduction in activity may also be called knockout or null mutant herein. |
| ackA | Gene encoding acetate kinase, required for synthesis of acetate from acetyl-CoA. |
| acr1 | Gene encoding a fatty aldehyde-forming acyl-CoA reductases from *Acinetobacter calcoaceticus* |
| acrM | Gene encoding a fatty aldehyde-forming acyl-CoA reductases from *Acinetobacter* sp. strain M-1 |
| adhE | Gene encoding aldehyde/alcohol dehydrogenase, required for synthesis of ethanol from acetyl-CoA |
| arcA | Encodes the cytosolic transcription factor of *E. coli*'s ArcAB two-component system, a global regulator of gene expression under microaerobic and anaerobic conditions. ArcAB regulates the expression of a large number of operons involved in respiratory and fermentative metabolism (including repression of fad regulon). |

-continued

| Abbreviation | Definition |
| --- | --- |
| arcB | Encodes the membrane associated sensor kinase and phosphatase of E. coli's ArcAB two-component system, a global regulator of gene expression under microaerobic and anaerobic conditions. ArcAB regulates the expression of a large number of operons involved in respiratory and fermentative metabolism (including repression of fad regulon). |
| atoB | Gene encoding an acetyl-CoA acetyltransferase |
| atoC | Encodes the cytosolic transcription factor of E. coli's AtoSC two-component system, which induces the ato operon (atoDAEB) for metabolism of short chain fatty acids in response to the presence of acetoacetate. |
| atoC(c) | atoC mutant that induces constitutive expression of the ato operon (atoDAEB) in the absence of acetoacetate. |
| atoS | Encodes the membrane associated sensor kinase of E. coli's AtoSC two-component system, which induces the ato operon (atoDAEB) for metabolism of short chain fatty acids in response to the presence of acetoacetate. |
| betA | Gene encoding choline dehydrogenase; used as a surrogate of alcohol dehydrogenase in the synthesis of n-alcohols |
| crp | Encodes transcriptional dual regulator CRP, which upon binding to its allosteric effector cyclic AMP (cAMP) regulate the expression of about 200 genes (most of them involved in the catabolism of carbon sources, including the fad regulon). |
| crp* | crp mutant encoding a cAMP-independent CRP (i.e. CRP*, which does not require cAMP to regulate gene expression and hence prevents catabolite repression of fad regulon in the presence of glucose) |
| cysJ | Gene encoding the flavoprotein subunit complex of sulfite reductase. Along with YdbK, CysJ could form a pyruvate: NADP oxidoreductase: we propose that ydbK and cysJ would encode the N-terminal pyruvate: ferredoxin oxidoreductase domain and the C-terminal NADPH-cytochrome P450 reductase domain, respectively. |
| Egter | Gene encoding an NAD(P)H-dependent transenoyl-CoA reductase from T. gracilis |
| eutE | Gene encoding predicted aldehyde dehydrogenase with high sequence similarity to adhE |
| eutG | Gene encoding predicted alcohol dehydrogenase |
| fadA | Gene encoding 3-ketoacyl-CoA thiolase (thiolase I), component of fatty acid oxidation complex |
| fadB | Gene encoding hydroxyacyl-CoA dehydrogenase, aka fused 3-hydroxybutyryl-CoA epimerase and delta(3)-cis-delta(2)-trans-enoyl-CoA isomerase and enoyl-CoA hydratase, part of fatty acid oxidation complex |
| fadBA | Both fadB and fadA |
| fadD | Gene encoding acyl-CoA synthetase (long-chain-fatty-acid--CoA ligase), part of fatty acyl-CoA synthetase complex |
| fadE | Gene encoding acyl-CoA dehydrogenase, a medium-long-chain fatty acyl-CoA dehydrogenase |
| fadI | Gene encoding 3-ketoacyl-CoA thiolase, part of fatty acid oxidation complex |
| fadJ | Gene encoding hydroxyacyl-CoA dehydrogenase, aka fused enoyl-CoA hydratase and epimerase and isomerase |
| fadK | Gene encoding short chain acyl-CoA synthetase |
| fadL | Gene encoding long-chain fatty acid outer membrane transporter |
| fadM | Gene encoding long-chain acyl-CoA thioesterase |
| fadR | Gene encoding a dual regulator of fatty acid metabolism, which exerts negative control over the fad regulon and positive control over expression of unsaturated fatty acid biosynthesis genes |
| fadR | fadR mutant that allows expression of the fad regulon in the absence of fatty acids |
| fnr | Gene encoding transcriptional dual regulator, regulates genes involved in the transition from aerobic to anaerobic growth |
| frdA | Gene encoding fumarate reductase, required for synthesis of succinate from fumarate |
| fucO | Gene encoding L-1,2-propanediol oxidoreductase |
| ldhA | Gene encoding lactate dehydrogenase |
| mgsA | Gene encoding methylglyoxal synthase; key enzyme in the synthesis of lactate through the methylglyoxal bypass |
| oleA | Gene encoding the enzyme that catalyzes non-decarboxylative Claisen condensation of CoA-thioesters in Xanthomonas campestris |
| oleB | Gene encoding a member of the α/β-hydrolase superfamily in Xanthomonas campestris |
| oleC | Gene encoding a member of the AMPdependent ligase/synthase superfamily or acetyl-CoA synthetase-like superfamily in Xanthomonas campestris |
| oleD | Gene encoding a member of the short-chain dehydrogenase/reductase superfamily in Xanthomonas campestris |
| paaJ | β-ketoadipyl-CoA thiolase catalyzing two beta-oxidation steps in phenylacetate catabolism |
| PCC7942_orf1593 | Gene encoding an aldehyde decarbonylase from Synechococcus elongatus PCC7942 |

-continued

| Abbreviation | Definition |
|---|---|
| pmAD | Gene encoding an aldehyde decarbonylase from *Prochlorococcus marinus* MIT9313 |
| poxB | Gene encoding pyruvate oxidase, which catalyzes the oxidative decarboxylation of pyruvate to form acetate, reduced ubiquinone (ubiquinol), and $CO_2$ |
| pta | Gene encoding phosphotransacetylase, required for synthesis of acetate from acetyl-CoA |
| Tdter | Gene encoding an NAD(P)H-dependent transenoyl-CoA reductase from *T. denticola* |
| tesA | Gene encoding multifunctional acyl-CoA thioesterase I and protease I and lysophospholipase L1 |
| tesB | Gene encoding thioesterase II |
| ucpA | predicted oxidoreductase, sulfate metabolism protein (used as surrogate of aldehyde-forming acyl Coenzyme A Reductase) |
| ybbO | predicted oxidoreductase with NAD(P)-binding Rossmann-fold domain (used as surrogate of aldehyde-forming acyl Coenzyme A Reductase) |
| yciA | Gene encoding acyl-CoA thioesterase |
| ydiL | Gene encoding fused predicted acetyl-CoA: acetoacetyl-CoA transferase: α subunit/β subunit |
| ydiO | Genes encoding predicted acyl-CoA dehydrogenase |
| ydiQ | Gene encoding putative subunit of YdiQ-YdiR flavoprotein |
| ydiR | Gene encoding putative subunit of YdiQ-YdiR flavoprotein |
| ydiS | Gene encoding putative flavoprotein |
| ydiT | Gene encoding putative ferredoxin |
| yiaY | Gene encoding predicted Fe-containing alcohol dehydrogenase |
| yqeF | Gene encoding predicted acetyl-CoA acetyltransferases |
| yqhD | Gene encoding NADP-dependent aldehyde/alcohol dehydrogenase |
| + | Refers to an overexpressed activity, meaning at least 150% wild type activity, and preferably 200, 500, 1000% or more. |

As used herein, references to cells or bacteria or strains and all such similar designations include progeny thereof. It is also understood that all progeny may not be precisely identical in DNA content, due to deliberate or inadvertent mutations that have been added to the parent. Mutant progeny that have the same function or biological activity as screened for in the originally transformed cell are included. Where distinct designations are intended, it will be clear from the context.

The terms "operably associated" or "operably linked," as used herein, refer to functionally coupled nucleic acid sequences.

As used herein "recombinant" is relating to, derived from, or containing genetically engineered material. In other words, the genome was intentionally manipulated in some way.

"Reduced activity" or "inactivation" is defined herein to be at least a 75% reduction in protein activity, as compared with an appropriate control species. Preferably, at least 80, 85, 90, 95% reduction in activity is attained, and in the most preferred embodiment, the activity is eliminated (100%, aka a "knockout" or "null" mutants). Proteins can be inactivated with inhibitors, by mutation, or by suppression of expression or translation, and the like. Use of a frame shift mutation, early stop codon, point mutations of critical residues, or deletions or insertions, and the like, can completely inactivate (100%) gene product by completely preventing transcription and/or translation of active protein.

"Overexpression" or "overexpressed" is defined herein to be at least 150% of protein activity as compared with an appropriate control species, and preferably 200, 500, 1000% or more. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or upregulating the endogenous gene, and the like.

The term "endogenous" or "native" means that a gene originated from the species in question, without regard to subspecies *or* strain, although that gene may be naturally or intentionally mutated, or placed under the control of a promoter that results in overexpression or controlled expression of said gene. Thus, genes from *Clostridia* would not be endogenous to *Escherichia*, but a plasmid expressing a gene from *E. coli* or would be considered to be endogenous to any genus of *Escherichia*, even though it may now be overexpressed.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", and "include" (and their variants) are open-ended linking verbs and allow the addition of other elements when used in a claim. "Consisting of" is closed, and "consisting essentially of" means that non-material elements can be added, such as background mutations that do not effect the reverse beta oxidation pathway, or differing media, buffers, salts, and the like.

As used herein "longer chain" alcohol, fatty acid and the like means 3 or more carbons, and preferably a 4 carbon or higher.

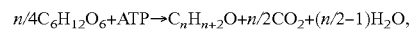
$$n/4C_6H_{12}O_6 + ATP \rightarrow C_nH_{n+2}O + n/2CO_2 + (n/2-1)H_2O,$$

with n being the chain length of the n-alcohol.

Figure 5:
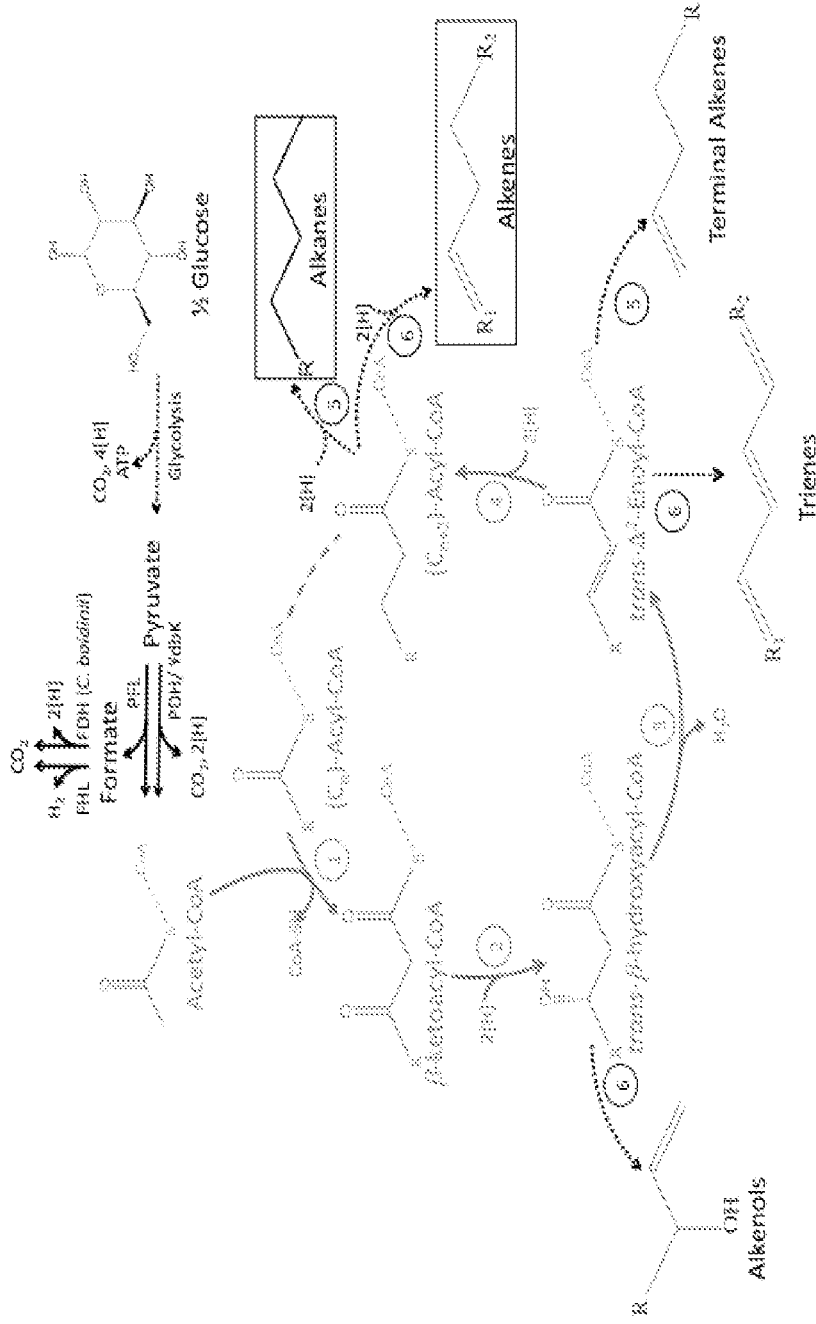

FIG. 5 is synthesis of hydrocarbons through engineered reversal of the β-oxidation cycle and efficient operation of the core pathway by optimal coupling of generation and consumption of reducing equivalents. Termination pathways "5" and "6" enable the synthesis of hydrocarbons from CoA-thioester intermediates using aldehyde-forming CoA thioester reductases and aldehyde decarbonylases (pathway "5", leading to the formation of alkanes or terminal alkenes of different chain lengths) and olefin-forming enzymes (pathway "6", leading to the formation of aliphatic internal alkenes or terminal alkenes or trienes or alkenols). Also noted are dissimilation of pyruvate through routes that preserve reducing equivalents (as opposed to releasing them in the form of hydrogen: e.g. PDH*, PNO, YdbK, NADH-dependent FDH), use of NAD(P)H-dependent trans-enoyl-CoA reductases (reaction 4), and direct coupling between trans-enoyl-CoA reduction (reaction 4) and pyruvate oxidation.

Figure 6:
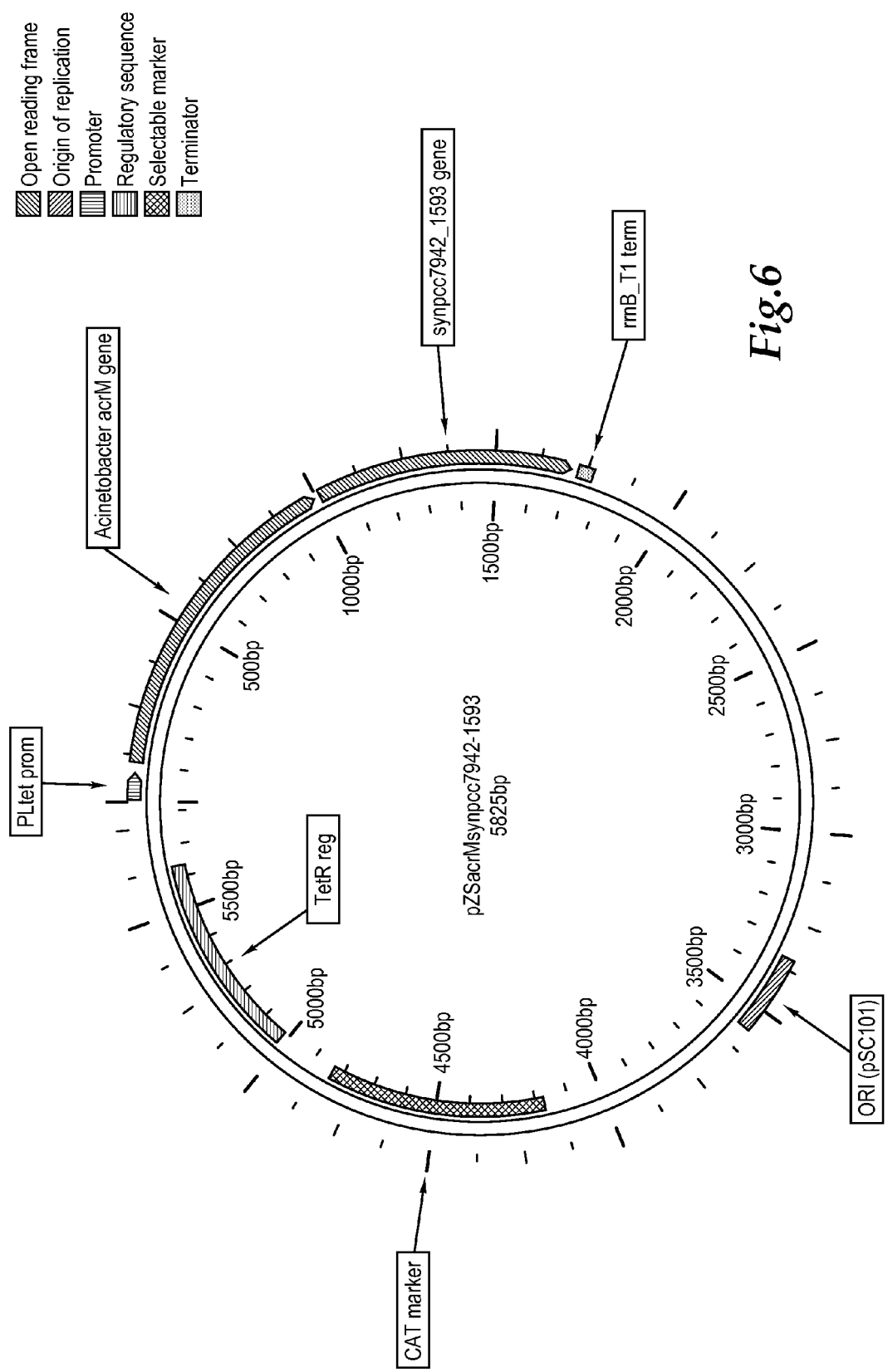

FIG. 6 is a diagram illustrating the map of plasmid pZS acrM synpcc7942_1593. This plasmid expresses codon optimized *Acinetobacter* acrM gene (encoding an aldehyde-forming CoA thioester reductase) and codon optimized *Synechococcus* synpcc7942_1593 gene (encoding an aldehyde decarbonylases). These two enzymes form a termination pathway that leads to the formation of alkanes or terminal alkenes of different chain lengths from the CoA-thioester intermediates of the β-oxidation reversal.

Figure 7A:
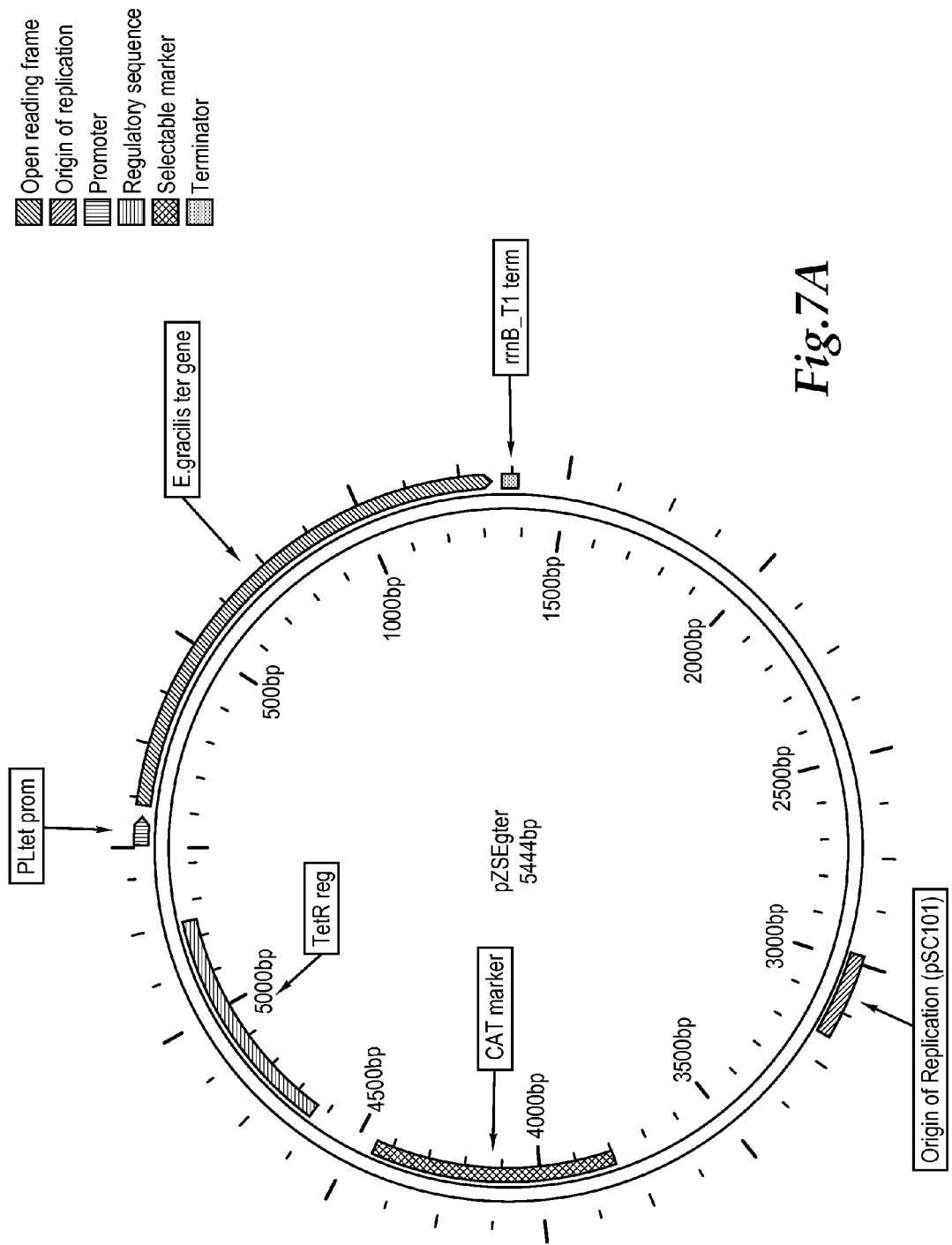
Figure 7B:
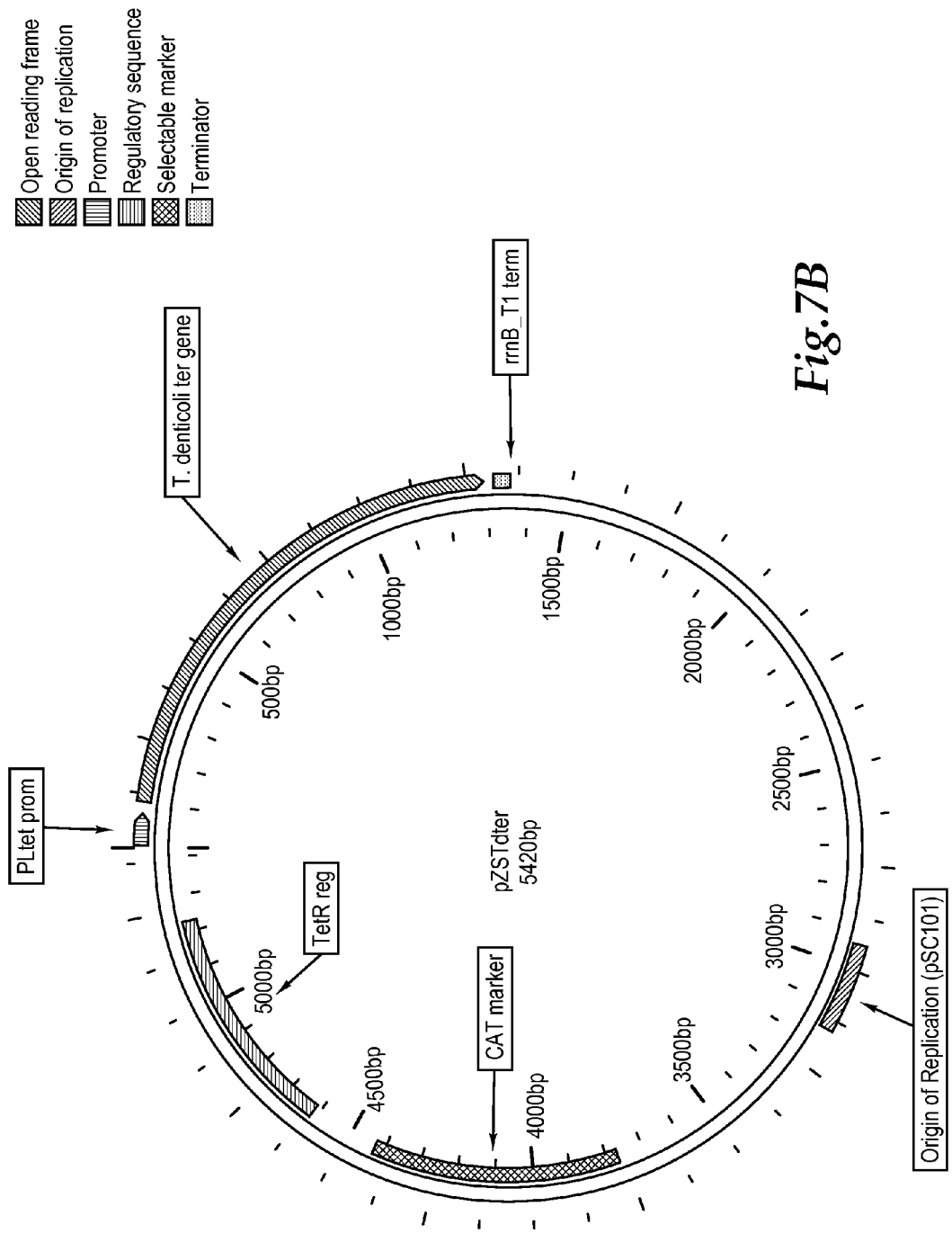

FIG. 7 contains diagrams illustrating the maps of plasmids pZS Egter (A) and pZS Tdter (B), carrying the genes that encode *E. gracilis* and *T. denticola* NAD(P)H-dependent transenoyl-CoA dehydrogenases, respectively.

Figure 8A:
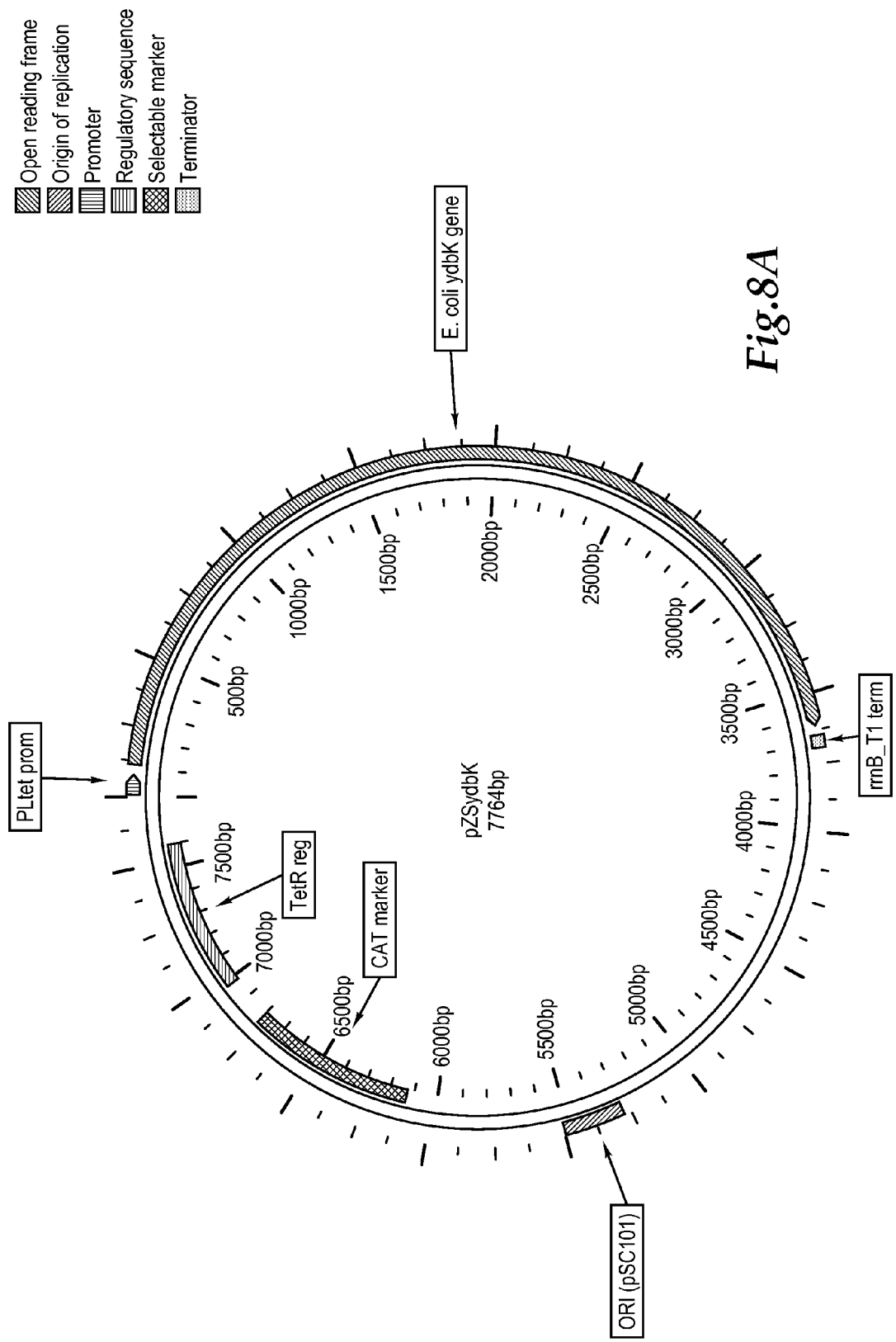
Figure 8B:
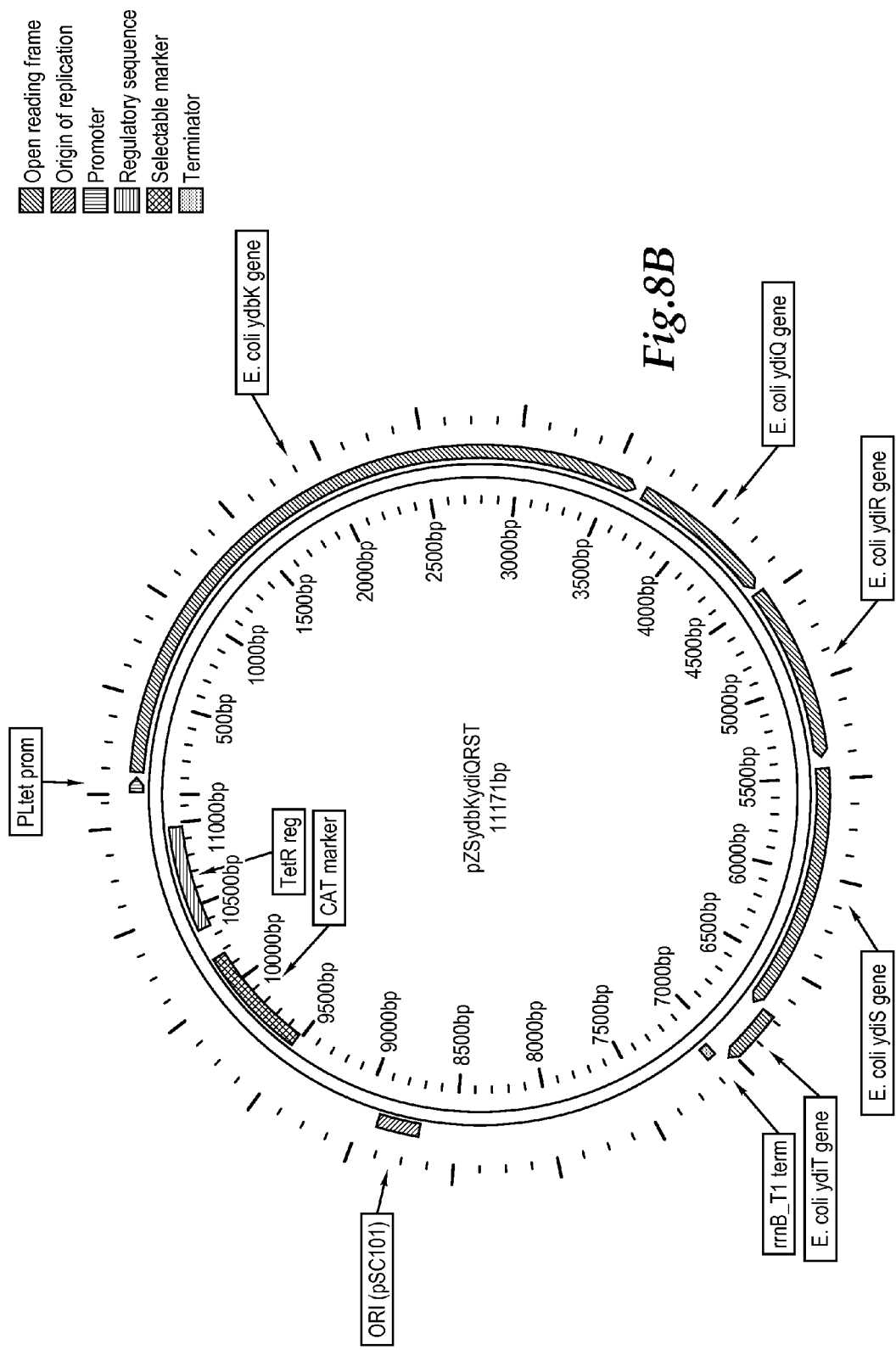
Figure 8C:
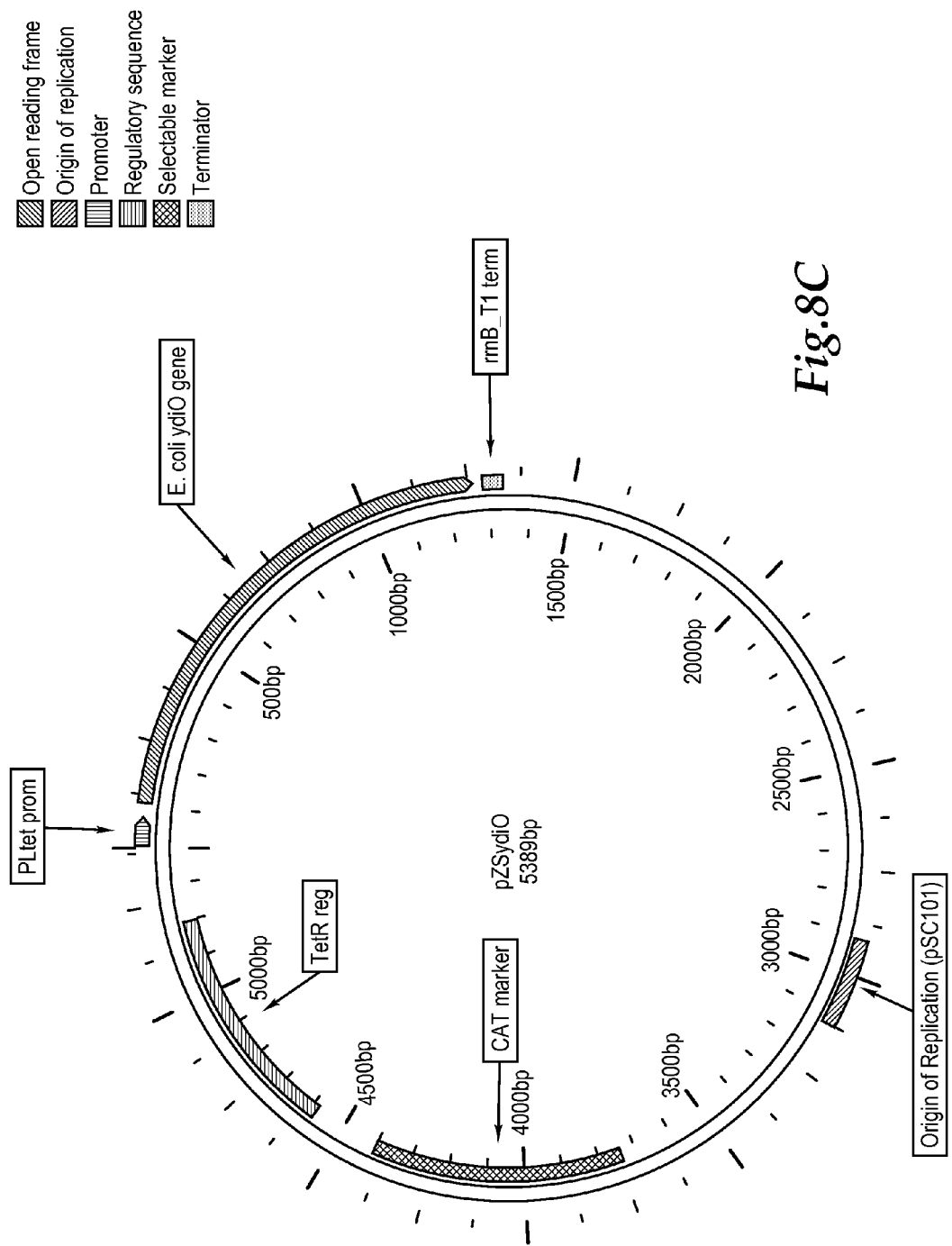

FIG. 8 contains diagrams illustrating the maps of plasmids pZS ydbK (A) pZS ydbKydiQRST (B), and pZS ydiO (C). These plasmids carry the genes that code for *E. coli* pyruvate:flavodoxin oxidoreductase (YdbK), acyl-CoA dehydrogenase (YdiO) and required electron transfer flavoproteins and ferredoxin (YdiQRST).

DESCRIPTION OF EMBODIMENTS OF THE INVENTION

We have engineered a functional reversal of the fatty acid oxidation cycle (aka β-oxidation) in *E. coli* and used it in combination with endogenous dehydrogenases and thioesterases to produce n-alcohols and fatty acids of different chain lengths (FIG. 1).

The engineered pathway operates with coenzyme-A (CoA) thioester intermediates and uses acetyl-CoA directly for acyl-chain elongation (rather than first requiring ATP-dependent activation to malonyl-CoA), features that enable product synthesis at maximum carbon and energy efficiency.

The synthesis of substituted and ubsubstituted n-alcohols and carboxylic acids (FIGS. 2 and 3) at yields and titers higher than previously reported demonstrate the superior nature of the engineered pathway. The ubiquitous nature of the n-oxidation cycle should enable the efficient synthesis of a host of non-native products in industrial organisms without recruiting foreign genes, an approach we term here homologous metabolic engineering.

We will shortly demonstrate the production of alkanes and alkenes using non-native enzymes added to the bacteria, and the vectors for same have already been constructed.

EXAMPLE 1

Materials and Methods

The material and methods detailed herein are exemplary only, but the techniques are standard in the art and different methodologies can be substituted herein. What is important is the engineering to effect pathway reversal, direct carbon flow, and upregulating the termination enyzmes.

Reagents

Chemicals were obtained from FISHER SCIENTIFIC™ (Pittsburgh, Pa.) and SIGMA-ALDRICH CO.™ (St. Louis, Mo.).

Culture Medium

The minimal medium designed by Neidhardt (1974) with $Na_2HPO_4$ in place of $K_2HPO_4$ and supplemented with 20 g/L glucose, 40 g/L calcium bicarbonate, 100 µM $FeSO_4$, 5 mM calcium pantothenate, 3.96 mM $Na_2HPO_4$, 5 mM $(NH_4)_2SO_4$, and 30 mM $NH_4Cl$ was used. Fermentations conducted in the SIXFORS™ multi-fermentation system also included 1 mM betaine.

Plasmid Construction

Standard recombinant DNA procedures were used for gene cloning, plasmid isolation, and electroporation. Manufacturer protocols and standard methods were followed for DNA purification (QIAGEN,™ CA, USA), restriction endonuclease digestion (NEW ENGLAND BIOLABS,™ MA, USA), and DNA amplification (STRATAGENE,™ CA, USA and INVITROGEN,™ CA, USA). For plasmid construction, genes were amplified from MG1655 genomic DNA using primers designed to create 15 bp of homology on each end of the gene insert for subsequent recombination into the desired plasmid. Plasmids were linearized using restriction endonuclease digestion, then recombined with the appropriate gene(s) using an IN-FUSION DRY-DOWN PCR CLONING KIT™ (CLONTECH,™ Mountain View, Calif., USA) and subsequently used to transform chemically competent FUSION BLUE™ cells (CLONTECH,™ Mountain View, Calif., USA).

Transformants that grew on LB plates containing the appropriate antibiotic were struck for isolation, and then subjected to preliminary screening by PCR. Colonies passing preliminary inspection were then individually grown for plasmid purification. Purified plasmids were confirmed to have the appropriate insert both by PCR as well as restriction endonuclease digest verification. Plasmids in each case include the plasmid promoter, a ribosomal binding site for each gene, MG1655 gene(s), and a plasmid terminator. Resulting plasmids (and strains) are listed in Tables 3 and 4.

Metabolite Identification

The identity of metabolic products was determined through one-dimensional (1D) proton nuclear magnetic resonance (NMR) spectroscopy. 60 µL of $D_2O$ and 1 µL of 600 mM NMR internal standard TSP [3-(trimethylsilyl) propionic acid-D4, sodium salt] were added to 540 µL of the sample (culture supernatant). The resulting solution was then transferred to a 5 mm-NMR tube, and 1D proton NMR spectroscopy was performed at 25° C. in a Varian 500-MHz Inova spectrometer equipped with a Penta probe (VARIAN, INC.,™ Palo Alto, Calif.) using the following parameters: 8,000-Hz sweep width, 2.8-s acquisition time, 256 acquisitions, 6.3-µs pulse width, 1.2-s pulse repetition delay, and presaturation for 2 s. The resulting spectrum was analyzed using FELIX™ 2001 software (ACCELRYS SOFTWARE INC.,™ Burlington, Mass.). Peaks were identified by their chemical shifts and J-coupling values, which were obtained in separate experiments in which samples were spiked with metabolite standards (2 mM final concentration).

Identification of n-alcohols was conducted through gas chromatography-mass spectroscopy (GC-MS) following a modification of the method reported by Atsumi (2008). The analysis was performed on an AGILENT™ 6890 GC/5973 MS (AGILENT TECHNOLOGIES,™ Palo Alto, Calif.) instrument with a HP-5 ms capillary column (30 m×0.25 mm×0.25 µm). 1 ml of supernatant of culture broth was extracted with 500 µl of GC standard grade hexane (Fluka). 0.5 µl of the extracted sample was injected using a 20:1 split at 250° C. The oven temperature was initially held at 75° C. for 2 min and then raised with a gradient of 5° C./min to 280° C. and held for 2 min. Helium (MATHESON TRI-GAS,™ Longmont, Colo.) was used as the carrier gas with a 14-lb/in² inlet pressure. The injector and detector were maintained at 255° C.

Identification of fatty acids was performed on a SHIMADZU™ Auto-System GC 2010 (SHIMADZU,™ Japan) equipped with a DB-5MS capillary column (30 m×0.25 mm×0.25 µm) and directly connected to MS. The following method was used: an initial temperature of 50° C. was held for 2 min and then ramped to 220° C. at 4° C. per min and held for 10 min². Extraction and derivatization procedures are described in section Metabolite Quantification.

Metabolite Quantification

The quantification of glucose, organic acids, ethanol, and butanol was conducted by high-performance liquid chromatography (HPLC). Samples (culture supernatant) were analyzed with ion-exclusion HPLC using a SHIMADZU™ Prominence SIL 20 system (SHIMADZU SCIENTIFIC INSTRUMENTS, INC.,™ Columbia, Md.) equipped with an HPX-87H organic acid column (BIO-RAD,™ Hercules, Calif.) with operating conditions to optimize peak separation (0.3 mL/min flowrate, 30 mM $H_2SO_4$ mobile phase, column temperature 42° C.).

Quantification of longer chain (C>4) n-alcohols was conducted through gas chromatography (GC) in a VARIAN™ CP-3800 gas chromatograph (VARIAN ASSOCIATES, INC.,™ Palo Alto, Calif.) equipped with a flame ionization detector (GC-FID). Sample extraction procedure was as described above in section Metabolite Identification. The separation of alcohol compounds was carried out using a VF-5ht column (15 m, 0.32 mm internal diameter, 0.10 µm film thickness; VARIAN ASSOCIATES, INC.,™ Palo Alto, Calif.). The oven temperature was initially held at 40° C. for 1 min and then raised with a gradient of 30° C./min to 130° C. and held for 4 min. The temperature was then raised with a gradient of 15° C./min to 230° C. and held for 4 min. Helium (1 ml min⁻¹, MATHESON TRI-GAS,™ Longmont, Colo.)

was used as the carrier gas. The injector and detector were maintained at 250° C. A 0.5-μl sample was injected in splitless injection mode.

Quantification of fatty acids was carried out in a VARIAN™ CP-3800 gas chromatograph (VARIAN ASSOCIATES, INC.,™ Palo Alto, Calif.) after hexane-methyl tertiary butyl ether (MTBE) extraction (Lalman 2004) and FA transesterification with a mixture of cholophorm:methanol: hydrochloric acid [10:1:1, vol/vol/vol] as previously reported (Dellomonaco 2010). The resulting fatty acids methyl esters were quantified according to the following method: 50° C. held for 1 min, 30° C./min to 160° C., 15° C./min to 200° C., 200° C. held for 1.5 min, 10° C./min to 225° C., and 225° C. held for 15 min.

Enzyme Assays

For measurement of enzymatic activities, cells from 24 hour shake flask cultures were washed twice with 9 g/L sodium chloride under anaerobic conditions and stored at −80° C. until use. Cell extracts for all assays were prepared as follows under anaerobic conditions. 40 units of $OD_{550\ nm}$ was re-suspended in 1 mL of 100 mM Tris-HCl buffer (pH 7.0) with 1 mM DTT. After cellular disruption using a DISRUPTOR GENIE™ (SCIENTIFIC INDUSTRIES, INC.,™ Bohemia, N.Y.), cellular debris was removed by centrifugation (13,000×g, 4° C., 10 min) and the supernatant used as cell extract. Absorbance changes for all assays were monitored in a BIOMATE™ 5 spectrophotometer (THERMO SCIENTIFIC,™ MA, USA). The linearity of reactions (protein concentration and time) was established for all assays and the non-enzymatic rates were subtracted from the observed initial reaction rates. Enzymatic activities are reported as μmol of substrate per minute per mg of cell protein and represent averages for at least three cell preparations. Protein concentration was measured using the Bradford assay reagent (THERMO SCIENTIFIC,™ MA, USA) with BSA as a standard.

Acetyl-CoA acetyltransferase (THL) activity was determined using acetoacetyl-CoA and CoA as substrates, and the decrease in acetoacetyl-CoA concentration was measured at 303 nm. β-Hydroxybutyryl-CoA dehydrogenase activity was measured at 340 nm by monitoring the decrease in NADH concentration resulting from β-hydroxybutyryl-CoA formation from acetoacetyl-CoA. Crotonase activity was measured by monitoring the decrease in crotonyl-CoA concentration at 263 nm, which results from β-hydroxybutyryl-CoA formation from crotonyl-CoA. Butyryl-CoA dehydrogenase activity was assayed in the direction of crotonyl-CoA reduction by monitoring the ferricenium ion at 300 nm, which acts as an electron donor. In addition, assays in which the ferricenium ion was replaced with 0.2 mM NAD(P)H and the absorbance measured at 340 nm were also run. Butyraldehyde dehydrogenase activity was assayed in the direction of butyraldehyde oxidation by monitoring $NAD(P)^+$ reduction at 340 nm. To measure butanol dehydrogenase activity, the decrease in NAD(P)H concentration resulting from butanol formation from butyraldehyde is monitored at 340 nm under anaerobic conditions at 30° C.

EXAMPLE 2

One-Turn Reversal of β-Oxidation Cycle

Given the applications of n-butanol as both advanced biofuels and building blocks for the chemical industry, we chose it as the first product to demonstrate the feasibility of engineering a functional reversal of the β-oxidation cycle as an efficient platform for fuel and chemical production (FIG. 1).

Figure 1A:
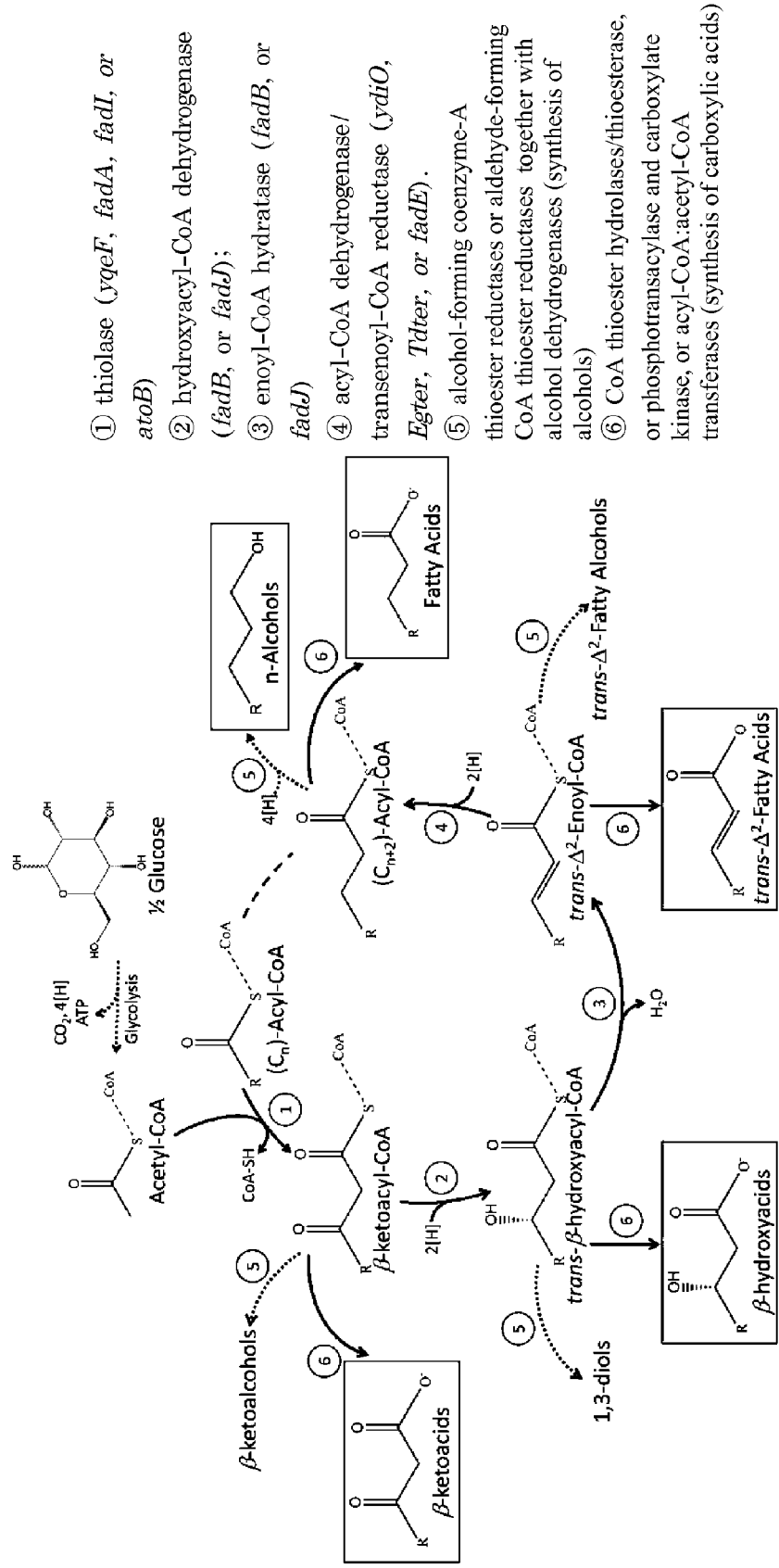
FIG. 1A Proposed metabolic platform for the combinatorial synthesis of advanced fuels and chemicals using a functional reversal of the β-oxidation cycle. The engineered reversal of the β-oxidation cycle reported in this work is composed of the following enzymes (gene names in parentheses): ① thiolase (yqeF, fadA, atoB); ② hydroxyacyl-CoA dehydrogenase (fadB, fadJ); ③ enoyl-CoA hydratase (fadB, fadJ) (note: ② and ③ are fused in this species); ④ acyl-CoA dehydrogenase (ydiO, fadE). Each turn of the reverse cycle generates an acyl-CoA that is two carbons longer than the initial acyl-CoA thioester (indicated as $C_{n+2}$). Intermediates in the engineered pathway can be converted to a functionally diverse set of alcohols and carboxylic acids of different chain lengths using one or more of i) alcohol-forming CoA thioester reductases or ii) aldehyde-forming CoA thioester reductases and alcohol dehydrogenases (⑤) or iii) CoA thioester hydrolases/thioesterases, or acyl-CoA:acetyl-CoA transferases, or phosphotransacylase and carboxylate kinases (⑥), as indicated. Products whose synthesis was demonstrated in this study are shown in boxes. Abbreviations: R indicates the side chain (e.g. R=H for acetyl-CoA and R=$CH_3$ for propionyl-CoA) attached to the acyl-CoA group of the primer or starter molecule. Dotted lines indicate multiple steps while dashed lines without arrowheads connect identical metabolites of different chain length. A comparison of n-alcohol production between the reversal of the β-oxidation cycle engineered in this work and the recently proposed fatty acid biosynthesis pathway[2] is shown in FIG. 4.

Synthesis of n-butanol can be realized through a one-turn reversal of the β-oxidation cycle in combination with native aldehyde/alcohol dehydrogenases (FIG. 1a, reactions ①-⑤). This engineered pathway represents an *E. coli* surrogate of the n-butanol pathway operating in *Clostridia*.

Given the specificity of atoB-encoded acetyl-CoA acetyltransferase for short-chain acyl-CoA molecules and the high sequence similarity between atoB and yqeF (predicted acyltransferase), these genes were selected for Reaction ① of the pathway. The next two steps can be catalyzed by 3-hydroxyacyl-CoA dehydrogenases and enoyl-CoA hydratases, encoded by fadB and fadJ (Reactions ② and ③ in FIG. 1a). The fourth step in this one-turn reversal of the β-oxidation cycle can be catalyzed by acyl-CoA dehydrogenase (fadE or ydiO) (Reaction ④).

Figure 1B:
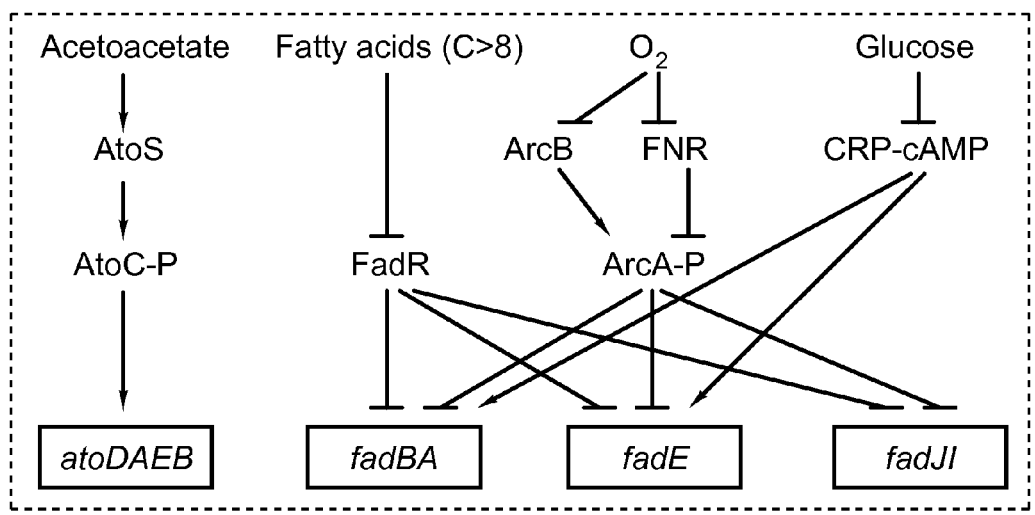
FIG. 1B Regulation of operons encoding the proposed reversal of the n-oxidation cycle by regulators FadR, ArcAB, FNR, CRP-cAMP, AtoSC. Activation and repression of operons is indicated by "↓" and "⊥", respectively.

The above genes are organized in four operons in the *E. coli* genome and are subjected to several levels of regulation (FIG. 1b). These regulatory pathways were therefore engineered to promote the reversal of the n-oxidation cycle.

Constitutive expression of fad and ato genes (regulated by FadR and AtoC, respectively: FIG. 1b) was achieved through fadR and atoC(c) mutations (Dellomonaco 2010). Since anaerobic/microaerobic conditions used in the production of fuels and chemicals would lead to repression of most target operons by ArcA (FIG. 1b), the arcA gene was also deleted.

Several operons of interest are also activated by the cyclic-AMP receptor protein (CRP)-cAMP complex (FIG. 1b) and are therefore subjected to carbon catabolite repression in the presence of glucose. This regulatory mechanism was circumvented by replacing the native crp gene with cAMP-independent mutant crp* (Eppler & Boos, 1999). While these genetic manipulations were predicted to enable expression of the β-oxidation cycle (FIG. 1b), no butanol synthesis was observed in strain fadR atoC(c) Δcrp crp* ΔarcA (RB01) or its parent fadR atoC(c) (Table 2). Table 5 provides details about mutations introduced at the crp, fadR, and atoSC loci.

Given the significant accumulation of other fermentation products (Table 2), the pathways involved in the synthesis of ethanol, acetate, and succinate were also blocked (ΔadhE, Δpta and ΔfrdA knockouts, respectively) in an attempt to channel carbon to the engineered pathway. Although the synthesis of these competing by-products was greatly reduced, strain RB02 (RB01 ΔadhE Δpta ΔfrdA) did not produce n-butanol either (Table 2).

Enzyme activity measurements confirmed a functional expression of the reversal of the β-oxidation cycle in strain RB02, compared to negligible activity in wild-type MG1655 (Table 1a). However, the levels of n-butanol dehydrogenase were very low (Table 1a), probably preventing n-butanol synthesis.

Figure 2A:
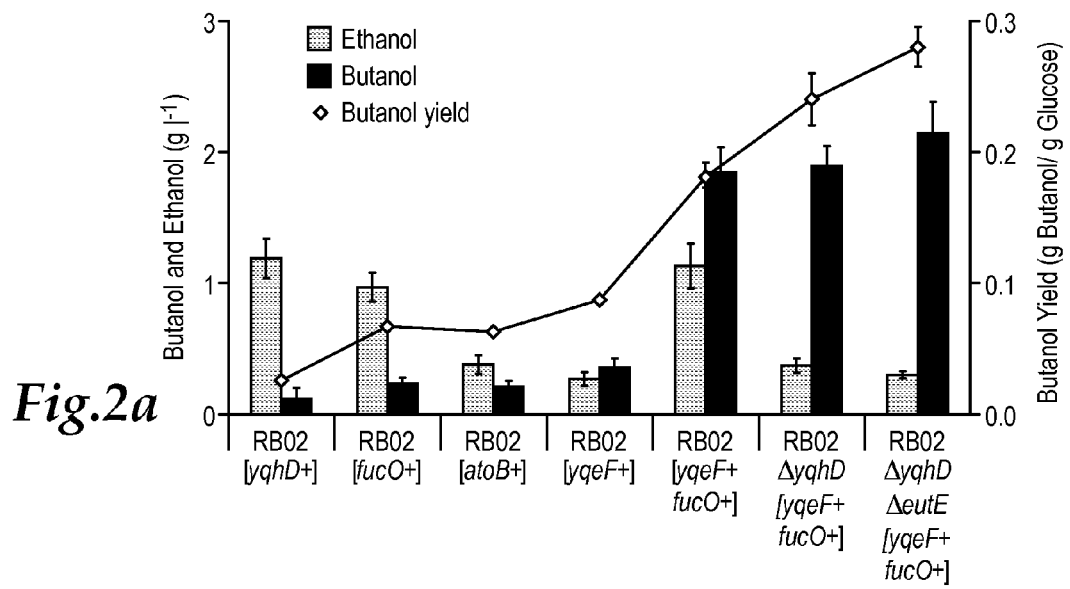
FIG. 2 Engineered one-turn reversal of the n-oxidation cycle for the synthesis of n-butanol and short-chain carboxylic acids. (a) Effect of gene overexpressions and knockouts (indicated underneath x axis) on the synthesis of n-butanol and ethanol in strain RB02 (fadR atoC(c) crp* ΔarcA ΔadhE Δpta ΔfrdA). Experiments were performed at 30° C. for 24 hours in shake flasks using glucose (1% w/v) minimal medium. The n-butanol yield was calculated as g n-butanol/g total glucose consumed. (b) Kinetics of n-butanol production by strain RB02 ΔyqhD ΔeutE [yqeF+fucO+]. Cells were cultivated in fermentors containing minimal medium supplemented with 5% (w/v) glucose. The dissolved oxygen was controlled at 5% of saturation, temperature at 30° C., and pH at 7. (c) Synthesis of β-ketobutyric (left panel), β-hydroxybutyric (center panel), and trans-2-butenoic (right panel) acids upon overexpression of thioesterases I (TesA) and II (TesB) in strains RB02, RB02ΔfadB, and RB02ΔydiO. Experiments were run at 37° C. for 48 hours in shake flasks using glucose (1% w/v) minimal medium.

To address this issue, two endogenous aldehyde/alcohol dehydrogenases with high sequence and structure similarity to the Clostridial butyraldehyde/butanol dehydrogenase were overexpressed in strain RB02: i.e. L-1,2-propanediol oxidoreductase (fucO) and an aldehyde/alcohol dehydrogenase (yqhD) (Table 7). Despite the potential for YqhD to catalyze the conversion of butyraldehyde to n-butanol, overexpression of fucO led to higher n-butanol titer and yield (FIG. 2a). Nonetheless, both enzymes proved functional and either or both could be used.

Although high levels of thiolase activity were observed in RB02 (Table 1a), these measurements account for enzymes with specificity for both short- and long-chain acyl-CoA molecules. In an attempt to divert acetyl-CoA to the n-butanol pathway, acetyl-CoA acetyltransferases that possess higher affinity for short-chain molecules (atoB and yqeF: FIG. 1a, Reaction ①) were overexpressed. The resulting strains, RB02 [atoB+] and RB02 [yqeF+], synthesized appreciable amounts of n-butanol (FIG. 2a).

Overexpression of yqeF, whose function in E. coli metabolism is currently unknown, yielded higher concentrations of n-butanol and lower concentrations of the major fermentation by-product ethanol (FIG. 2a). No n-butanol synthesis was observed upon overexpression of atoB or yqeF in wild-type MG1655.

Based on the above results, an increased partition of carbon flux towards n-butanol should be realized by simultaneous overexpression of yqeF, to channel acetyl-CoA into the engineered reversal of the β-oxidation cycle, and fucO, to improve the conversion of butyryl-CoA to n-butanol. Indeed, strain RB02 [yqeF+fucO+] produced significant amounts of n-butanol (1.9 g/L) at a high n-butanol-to-ethanol ratio (>5:1) (FIG. 2a). No n-butanol production was observed upon simultaneous overexpression of yqeF and fucO in the wild-type background or in a strain containing pta, adhE, and frdA deletions, underscoring the importance of the fadR atoC(c) Δcrp crp* ΔarcA genotype.

Since the engineering of strain RB02 [yqeF+fucO+] involved manipulation of several global regulators with potential pleiotropic effects, a characterization of the proposed reversal of the β-oxidation cycle was conducted to establish its role on n-butanol synthesis (Table 1). Activity measurements showed high level of expression of key enzymes involved in the postulated pathway in strain RB02 [yqeF+fucO+] and negligible activity in wild type MG1655 (Table 1a). Gene knockout and gene complementation experiments along with quantification of fermentation products (Table 1b) demonstrated that the primary genes involved in the synthesis of n-butanol through the engineered one-turn reversal of the β-oxidation pathway are (encoded activity in parenthesis): yqeF (predicted acyltransferase), fadB (3-hydroxyacyl-CoA dehydrogenase and enoyl-CoA hydratase), ydiO (predicted acyl-CoA dehydrogenase), and fucO (L-1,2-propanediol oxidoreductase/n-butanol dehydrogenase).

YdiO is proposed to catalyze the reduction of enoyl-CoA to acyl-CoA (Reaction ④). The reverse of this reaction is catalyzed by FadE and is the only irreversible step in the catabolic operation of the β-oxidation cycle[5]. In agreement with our proposal, deletion of ydiO in strain RB02 [yqeF+fucO+] completely abolished n-butanol synthesis (Table 1b). Although ydiO was previously proposed to encode an acyl-CoA dehydrogenase that would replace FadE during the anaerobic catabolism of fatty acids[20], a sequence comparison between YdiO and E. coli proteins does not reveal a significant similarity to FadE (Table 9). In contrast, YdiO shares high homology with crotonobetainyl-CoA reductase (CaiA). CaiA catalyzes the reduction of crotonobetainyl-CoA to γ-butyrobetainyl-CoA, a reaction similar to that catalyzed by YdiO in the reversal of the β-oxidation cycle. Moreover, the operon fixABCX is required for the transfer of electrons to CaiA and encodes flavoproteins and ferredoxin with high sequence similarity to YdiQRST (Table 9). This analysis suggests that ferredoxin and flavoproteins encoded by ydiQRST are involved in the transfer of electrons to YdiO during the reduction of enoyl-CoA to acyl-CoA. Standard Gibbs energy calculations revealed that the engineered reversal of the β-oxidation cycle is thermodynamically feasible if ferredoxin is the source of reducing power for the conversion of enoyl-CoA to acyl-CoA (Table 10). We then propose that the reduction of enoyl-CoA to acyl-CoA is mediated by YdiO-YdiQRST.

Figure 2B:
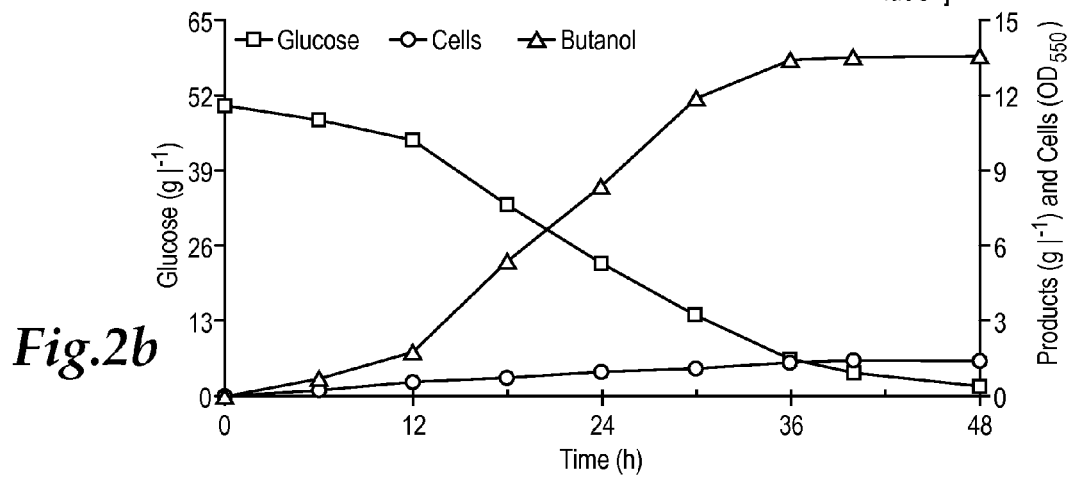

Further reduction in the synthesis of by-product ethanol, and hence an increase in n-butanol yield, were realized by combining the overexpression of fucO and yqeF with the deletion of yqhD and eutE (aldehyde dehydrogenase with high sequence similarity to adhE). The resulting strain (RB02 ΔyqhD ΔeutE [yqeF+fucO+]) synthesized 2.2 g/L of n-butanol in 24 hours at a yield of 0.28 g n-butanol/g glucose (FIG. 2a). When grown in a bioreactor using a higher initial concentration of glucose, this strain produced n-butanol at high titer (~14 g/L), yield (0.33 g n-butanol/g glucose) and rate (~2 g n-butanol/g cell dry weight/h) (FIG. 2b).

This performance, which was achieved without importing foreign genes and in the absence of rich nutrients, is an order of magnitude better than reported for any other organism engineered for n-butanol production and also surpasses the yield and specific productivity reported for native n-butanol producers. The reversal of the β-oxidation cycle engineered in this strain operated at a maximum carbon flux of 73.4 mmol acetyl-CoA/g cell dry weight/h (12-18 hours in FIG. 2b), which exceeds the flux reported in the literature for native or engineered fermentative pathways. Taken together, these results demonstrate that the engineered reversal of the β-oxidation pathway is a superior metabolic platform for the production of fuels and chemicals and can support the efficient synthesis of non-native products in industrial organisms without recruiting foreign genes (i.e. endogenous metabolic engineering).

Figure 2C:
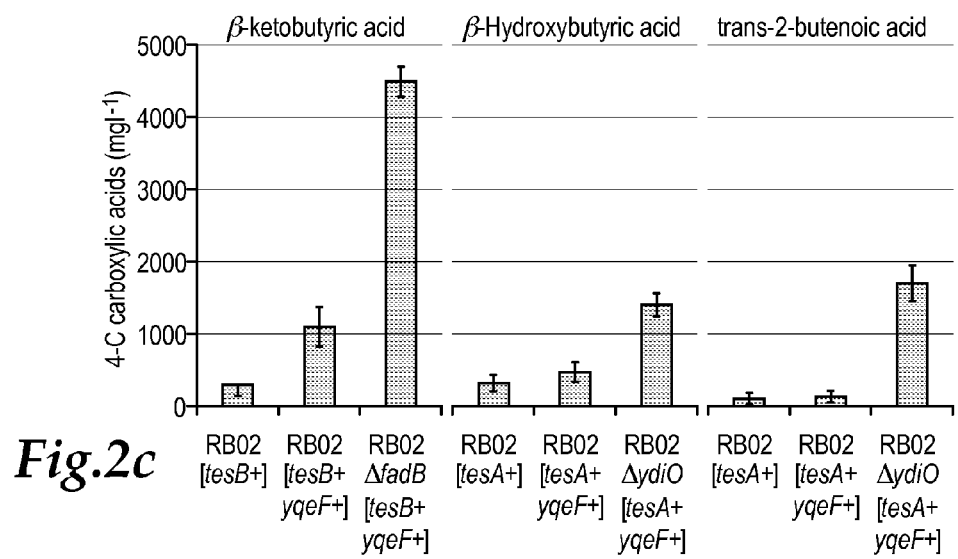

The engineered reversal of the β-oxidation cycle generates a diverse set of CoA thioester intermediates that can be converted to the corresponding alcohols and carboxylic acids (FIG. 1A). To illustrate product synthesis from intermediates other than acyl-CoA, we used thioesterase I (TesA) and thioesterase II (TesB) as termination enzymes. Small amounts of 3-hydroxybutyric, 3-ketobutyric, and trans-2-butenoic acids were produced when these thioesterases were overexpressed in strain RB02 (FIG. 2c). The level of these products was significantly increased by simultaneous overexpression of thioesterase and yqeF-encoded short-chain acyltransferase (FIG. 2c). Further increases in product titer were realized upon deletion of fadB (~500 mg/L 3-ketobutyric acid) and ydiO (~150 mg/L and 200 mg/L of 3-hydroxybutyric and trans-2-butenoic acids, respectively) (FIG. 2c).

EXAMPLE 3

Making Longer Chains (C>4)

The operation of multiple cycles of the engineered reversal of the β-oxidation pathway, and hence the synthesis of CoA-thioester intermediates (and products) of longer chain length (C>4), can be facilitated by the overexpression of FadA, a 3-ketoacyl-CoA thiolase that is part of the β-oxidation complex (FadBA) and which possesses broad chain length specificity.

Figure 3A:
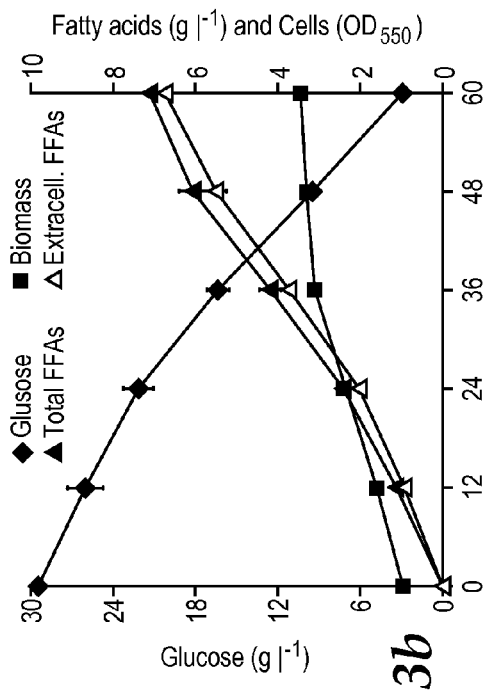
FIG. 3 Synthesis of higher-chain (C>4) carboxylic acids (a and b) and n-alcohols (c and d) through the engineered reversal of the n-oxidation cycle. (a) Accumulation of long-chain (C>10) free fatty acids in the extracellular medium of strain RB03 [fadBA+] upon overexpression of different thioesterases (FadM, YciA, TesA, TesB). Product yield is shown above the bars (g free fatty acid/g total glucose consumed×100). Experiments were run at 37° C. for 48 hours in shake flasks using glucose (2% w/v) minimal medium. (b) Kinetics of fatty acid synthesis by strain RB03 [fad-BA.fadM+]. Cells were cultivated in fermentors using glucose (3% w/v) minimal medium. The dissolved oxygen was controlled at 2% of saturation, temperature at 37° C., and pH at 7. (c) Synthesis of n-alcohols in strain RB03 [fadBA+] upon overexpression of alcohol dehydrogenases (YiaY, BetA, and EutG). Product yield is shown above the bars (g n-alcohol/g total glucose consumed×100). Experiments were run at 37° C. for 48 hours in shake flasks using glucose (2% w/v) minimal medium. (d) Effect of alcohol dehydrogenase overexpression (YiaY, BetA, and EutG) on the chain-length distribution of n-alcohols synthesized by strain RB03 [fadBA+] in the presence of 0.5 g/L propionate. Experiments were conducted as described in panel "c".

Overexpression of FadBA in conjuction with thioesterases (TesA, TesB, FadM or YciA) in strain RB03 (RB02ΔyqhDΔfucO ΔfadD) resulted in the accumulation of long-chain fatty acids in the extracellular medium (FIG. 3a). The fadD knockout in strain RB03 prevents re-utilization of the synthesized fatty acids. The choice of thioesterase allowed control over both length and functionality of the fatty acid side chain. For example, C16 and C18 saturated fatty acids were the only products when FadM was overexpressed while YciA and TesA overexpression supported the synthesis of 3-hydroxy (C14:3OH) and unsaturated (C18:1) fatty acids, respectively (FIG. 3a).

Figure 3B:
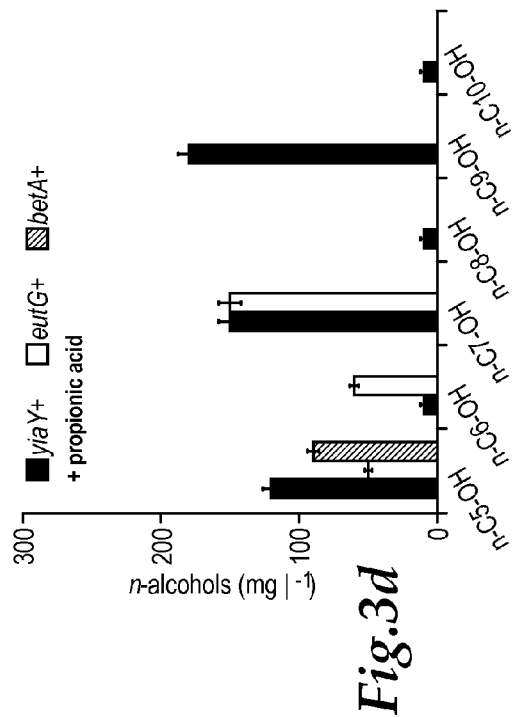

When grown in a bioreactor using a higher initial concentration of glucose, strain RB03 [fadBA.fadM+] produced long-chain extracellular fatty acids at high titer (~7 g/L) and yield (0.28 g fatty acids/g total glucose consumed) using a mineral salts medium without rich nutrients (FIG. 3b). These results are better than reported previously using an engineered fatty acid biosynthesis pathway (Table 9). No production of extracellular free fatty acids was observed upon overexpression of FadM in strain MG1655 ΔadhE Δpta ΔfrdA ΔfadD (Table 6C), demonstrating the requirement of an active reversal of the β-oxidation cycle. Measurements of total free fatty acids (i.e. extracellular+intracellular) in strain RB03 [fadBA.fadM+] and the corresponding controls showed that the engineered reversal contributed to the synthesis of 90-95% of the total free fatty acids (Table 6C).

Figure 3C:
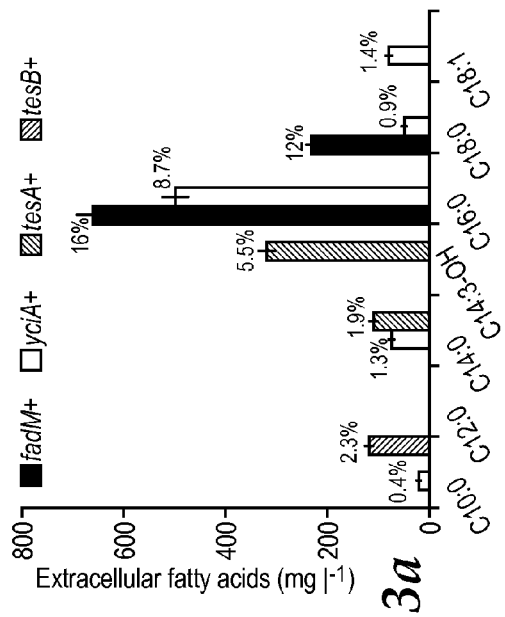

The synthesis of longer-chain (C>4) n-alcohols was also demonstrated by overexpressing the appropriate termination enzymes (FIG. 3c). We identified native enzymes that could serve as potential surrogates for the aldehyde-forming acyl-CoA reductases and alcohol dehydrogenases present in organisms that synthesize higher-chain linear n-alcohols (Table 7). The product titer (0.33 g/L) and yield (8.3% w/w) achieved upon overexpression of YiaY were higher than previously reported (Table 8).

Figure 3D:
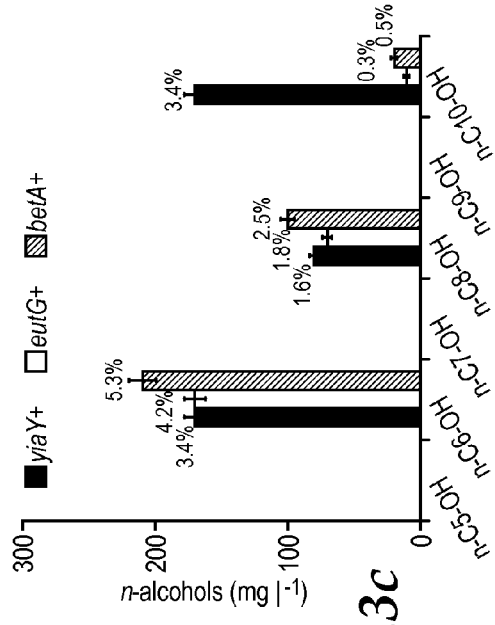

Synthesis of odd-chain n-alcohols was demonstrated by supplementing the medium with propionate as the precursor of propionyl-CoA (R=$CH_3$ in FIG. 1A). A clear shift in the distribution of n-alcohols was observed: odd-chain alcohols 1-pentanol, 1-heptanol, and 1-nonanol appeared as fermentation products and the synthesis of even-chain alcohols significantly decreased (FIG. 3d).

EXAMPLE 4

Synthesis of Alkanes/Alkenes

The CoA-thioester intermediates generated by the reversal of the β-oxidation cycle can be converted to alkanes by a two-step pathway composed of an aldehyde-forming fatty-AcylCoA reductase and a fatty aldehyde decarbonylase (FIG. 5). Olefins, on the other hand, will also be synthesized from acyl-CoAs via a pathway that uses a "head-to-head" condensation mechanism followed by reduction and decarbonylation steps.

Alkane-Biosynthesis Pathway:

A two-step pathway will be used, which involves the reduction of acyl-CoA to fatty aldehydes by the action of fatty aldehyde-forming acyl-CoA reductases followed by the decarbonylation of the resulting aldehyde to alkane by aldehyde decarbonylases (FIG. 5). This pathway is different from a recently reported pathway for the synthesis of alkanes from fatty-acyl-ACP (acyl-acyl carrier protein). Our pathway uses an acyl-CoA reductase as opposed to the reported acyl-ACP reductase. We have already used native fatty aldehyde-forming acyl-CoA reductases in the synthesis of fatty alcohols. In addition, we will use heterologous fatty aldehyde-forming acyl-CoA reductases from *Acinetobacter calcoaceticus* (acr1) and *Acinetobacter* sp. strain M-1 (acrM) (Ishige et al., 2002).

While both enzymes are active with a range of acyl-CoAs, the activity towards palmitoyl-CoA is very high: this is an important aspect because our strains engineered to produce fatty acids synthesize palmitic acid as the primary product (FIG. 3b), indicating the availability of palmitoyl-CoA for the fatty aldehyde-forming acyl-CoA reductases.

For the second step of the pathway we will use an aldehyde decarbonylase from *Synechococcus elongatus* PCC7942 (PCC7942_orf1593) and other orthologs recently reported by Schirmer (2010).

Genes encoding the aforementioned enzymes were clustered in the same expression vector (FIG. 6), which will be transformed into strains that we have already shown to be able to produce long-chain fatty acids from acyl-CoAs. Heterologous genes were codon-optimized for expression in *E. coli*. The effect of the expression levels of each enzyme in the pathway will be assessed through the use of different expression vectors, promoters and ribosomal binding sites, etc. Once alkane production has been verified, the vector carrying the alkane-biosynthesis pathway (FIG. 6) will be expressed in conjunction with a second vector carrying the β-oxidation enzymes.

The activity of proteins encoded by cloned genes will be quantified and the corresponding reactions characterized using in vitro analysis of enzyme kinetics and identification of reaction substrates and products using biochemical assays and NMR spectroscopy. Substrates with different chain length will be used in these assays.

Olefin-Biosynthesis Pathway:

The best-characterized pathway for the synthesis of olefins proceeds through a mechanism known as "head-to-head" condensation of acyl-CoAs and leads to the synthesis of long-chain olefins (C21-C31) with internal double bonds at the median carbon.

The optimal functioning of this pathway will require the expression of the cluster of olefin-forming enzymes OleABCD from bacteria such as *Xanthomonas campestris*. Recent in vitro studies have shown that OleA catalyzes the condensation of fatty acyl groups in the first step of the pathway through a non-decarboxylative Claisen condensation mechanism. Purified OleA was shown to be active with fatty acyl-CoAs that ranged from C8 to C16 in length, with maximum activity towards palmitoyl-CoA. The other three genes encode a member of the α/β-hydrolase superfamily (OleB), a member of the AMPdependent ligase/synthase superfamily or acetyl-CoA synthetase-like superfamily (OleC), and a member of the short-chain dehydrogenase/reductase superfamily (OleD).

The genes acyl, acrM, PCC7942 orf1593, oleABCD will be cloned in one expression vector and the effect of the expression levels of each enzyme in the pathway will be assessed through the use of different promoters and ribosomal binding sites, as described above. A second vector will be used to express the β-oxidation enzymes. The vectors will be transformed into strains already shown to be able to produce long-chain fatty acids from acyl-CoAs. The activity of proteins encoded by the cloned genes will be quantified and the corresponding reactions characterized using in vitro analysis of enzyme kinetics and identification of reaction substrates and products using biochemical assays and NMR spectroscopy.

EXAMPLE 5

Improving Efficiency of Reversed Cycle

The synthesis and consumption of reducing equivalents is a key aspect for the efficient operation of the engineered pathway, we propose to improve its functioning by manipulating the enzymes responsible for trans-enoyl-CoA reduction and pyruvate oxidation (FIG. 1A and FIG. 5). This includes dissimilation of pyruvate through routes that preserve reducing equivalents (as opposed to releasing them in the form of hydrogen), use of NAD(P)H-dependent trans-enoyl-CoA reductases, and direct coupling between trans-enoyl-CoA reduction and pyruvate oxidation.

Pyruvate can be converted to acetyl-CoA in *E. coli* through three main routes (FIG. 5): i) pyruvate formate-lyase (PFL), which generates formate as co-product, ii) pyruvate dehydrogenase (PDH), which generates $CO_2$ and NADH, and iii) a YdbK, a predicted pyruvate:flavodoxin oxidoreductase, that also generates $CO_2$ and transfer the electrons to the quinone pool. While the formate generated by PFL can be disproportionated to $CO_2$ and hydrogen by the action of formate hydrogenlyase (FHL), this enzyme does not generate NAD(P)H.

To address this issue, we will replace the native hydrogen-evolving FHL complex with an NAD-dependent formate dehydrogenase (FDH) from *C. boidinii* (FIG. 5). PDH and YdbK generate reducing equivalents in a form potentially usable by the engineered reversal of the b-oxidation pathway. However, effective functioning of PDH would require the use of anaerobic conditions or the replacement of the native PDH with an anaerobically active pyruvate dehydrogenase complex (PDH*) (Kim et al., 2007). In the case of YdbK, we propose the direct coupling of pyruvate oxidation and YdiO-catalyzed reduction of trans-enoyl-CoA. We will also evaluate the expression of a heterologous pyruvate-NADP oxidoreductase (PNO) from the mitochondrion of *Euglena gracilis* and from the apicomplexan *Cryptosporidium parvum*, which convert pyruvate to acetyl-CoA, $CO_2$, and NADPH (Rotte et al., 2001).

Two enzymes will be evaluated for the reduction of trans-enoyl-CoA, namely NAD(P)H-dependent trans-enoyl-CoA reductase from *Euglena gracilis* (Hoffmeister et al., 2005) and predicted *E. coli* acyl-CoA dehydrogenase (YdiO). In the case of YdiO, we have recently shown that this enzyme is required for the operation of the reversal of the b-oxidation pathway (Dellomonaco et al., 2011). The effect of availability of reducing equivalents in the form of NADPH or NADH will also be evaluated through manipulation of the flux through transhydrogenases as well as the carbon flux partitioning between Embden-Meyerhof-Parnas pathway, Pentose Phosphate pathway, and the Entner-Doudoroff pathway.

Genes encoding some of the aforementioned enzymes have been cloned in appropriate expression vectors (FIG. 7 and FIG. 8) and will be transformed into strains able to produce alcohols, carboxylic acids, alkanes, and alkenes via a an engineered reversal of the β-oxidation cycle. The encoded activities and corresponding reactions will be characterized using in vitro analysis of enzyme kinetics and identification of reaction substrates and products using biochemical assays and NMR spectroscopy.

Conclusions:

The functional reversal of the β-oxidation cycle engineered in this work represents a new and highly efficient platform for the synthesis of advanced fuels and chemicals. Its superior nature is illustrated in the following balanced equation for the synthesis of n-alcohols from glucose: $n/4C_6H_{12}O_6 \rightarrow C_nH_{n+2}O+n/2CO_2+(n/2-1)H_2O+n/2$ ATP, with n being the chain length of the n-alcohol (FIG. 1a). As can be seen, the engineered pathway has the potential to achieve the maximum yield of n-alcohols on glucose (66.7%, C-mole basis) and generates 1 ATP per each 2-C incorporated into the n-alcohol molecule. This ATP yield is equivalent to that of efficient homo-fermentative pathways found in nature such as ethanol and lactic acid fermentations. The high carbon and energy efficiency of the engineered reversal of the β-oxidation cycle is possible because it uses acetyl-CoA directly as C2 donor during chain elongation (as opposed to first requiring ATP-dependent activation to malonyl-CoA) and it functions with acyl-CoA intermediates, which are the precursors of alcohols and other important products (FIG. 1a).

Figure 4:
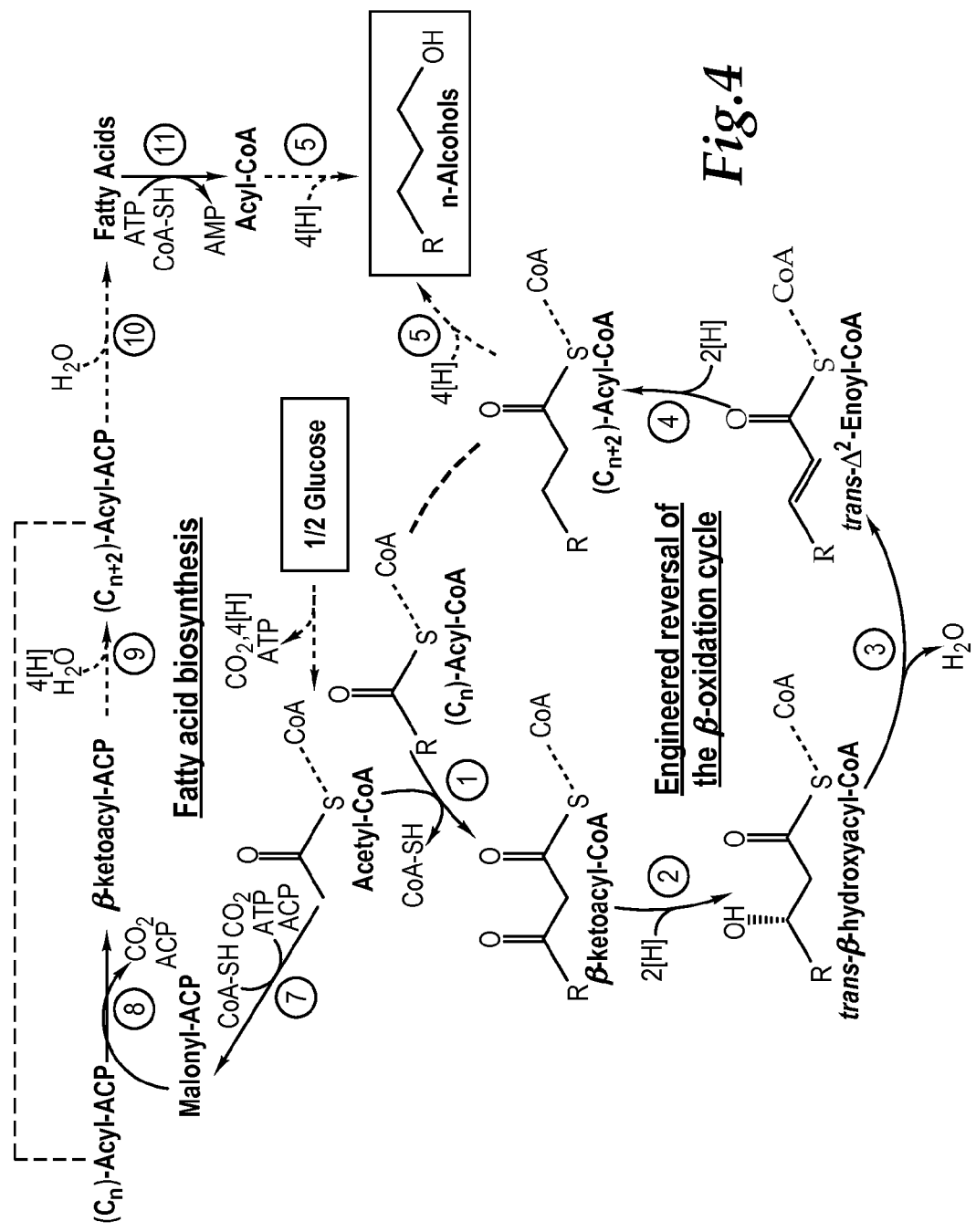
FIG. 4 is a comparison of n-alcohol synthesis via the fatty acid biosynthesis pathway (top) and the engineered reversal of the β-oxidation cycle (bottom). Reactions ①-⑤ are as indicated in FIG. 1. The fatty acid biosynthesis pathway uses acyl-ACP intermediates and involves a β-ketoacyl-acyl-carrier protein synthase (⑧) along with a 3-ketoacyl reductase, an enoyl reductase, and a 3-hydroxyacyl dehydratase (⑨). The synthesis of malonyl-ACP, the 2-C donor during chain elongation in fatty acid biosynthesis, is also shown (⑦). Production of n alcohols from these acyl-ACP intermediates requires their conversion to free acids (⑩) and acylation (⑪) before their reduction to alcohols (⑥) can be achieved. The use of acyl-ACP intermediates and malonyl-ACP as the 2-C donor during chain elongation in the fatty acid biosynthesis pathway limits its ATP efficiency, making it an ATP-consuming pathway, as shown in the following balanced equation for n-alcohol synthesis from glucose.

The synthesis of n-alcohols through alternative metabolic routes, such as the fatty acid biosynthesis and keto-acid pathways, is less efficient. For example, the use of the fatty acid biosynthesis pathway results in the net consumption of 1 ATP per molecule of n-alcohol synthesized (FIG. 4). This inefficiency is due to the consumption of ATP in the synthesis of malonyl-ACP (reaction ⑦ in FIG. 4), the C2 donor for chain elongation, and the use of acyl-ACP intermediates, which need to be converted to free acids and acylated (another ATP-consuming step) before their reduction to alcohols can be achieved (reactions ⑩ and ⑪ in FIG. 4). The recently proposed keto-acid pathway is also less efficient than the reversal of the β-oxidation cycle: e.g. the maximum theoretical yield of n-hexanol, the highest-chain linear n-alcohol reported with the keto-acid pathway, is only 50% C-mole (2 Glucose$\rightarrow$n-hexanol+ATP+2[H]+$6CO_2$).

While the work reported here focused on the engineering of *E. coli*, the ubiquitous nature of β-oxidation, aldehyde/alcohol dehydrogenase, and thioesterase enzymes will certainly enable the use of native metabolic engineering strategies to achieve the efficient synthesis of β-alcohols and fatty acids in other industrial organisms. A functional reversal of the β-oxidation cycle also holds great promise for the combinatorial biosynthesis of a wide range of molecules of various chain lengths and functionalities. For example, thioesterases and aldehyde/alcohol dehydrogenases can also act on the other thioester intermediates of the engineered pathway to generate a host of products such as β-keto acids and β-keto alcohols, β-hydroxy acids and 1,3-diols, and trans-$\Delta^2$-fatty acids and trans-$\Delta^2$-alcohols (FIG. 1a), as well as alkanes and alkenes (FIG. 5).

TABLE 1

Functional characterization of the engineered reversal of the β-oxidation cycle during the synthesis of n-butanol Table 1a. Activities of β-oxidation and butanol dehydrogenase enzymes in wild-type and engineered strains

| Strain | Enzyme activity (μmol/mg protein/min) ± standard deviation | | | |
|---|---|---|---|---|
| | THL[a] | HBD[a] | CRT[a] | BDH[a] |
| MG1655 | n.d. | 0.002 ± 0.000 | n.d. | 0.014 ± 0.001 |
| RB02[b] | 0.310 ± 0.079 | 0.304 ± 0.032 | 0.339 ± 0.049 | 0.004 ± 0.002 |
| RB02 [yqeF+ fucO+] | 0.498 ± 0.036 | 0.292 ± 0.013 | 0.334 ± 0.017 | 0.298 ± 0.020 |

TABLE 1-continued

Functional characterization of the engineered reversal of the β-oxidation cycle during the synthesis of n-butanol Table 1b. Butanol synthesis, glucose utilization, and cell growth in strain RB02 and its derivatives[c]

| Strain[d] | Butanol produced Yield (g/g) Concentration (g/L) | | Glucose utilized (g/L) | Cell growth (g/L) |
|---|---|---|---|---|
| RB02 [yqeF+ fucO+] | 0.182 | 1.85 | 10.19 | 0.72 |
| Reaction ①: yqeF (predicted acyltransferase) | | | | |
| RB02 ΔyqeF [fucO+] | 0.019 | 0.10 | 5.19 | 0.32 |
| RB02 [fucO+] | 0.063 | 0.23 | 3.66 | 0.41 |
| RB02 ΔyqeF [fucO+ yqeF+] | 0.159 | 1.11 | 7.00 | 0.43 |
| Reactions ② and ③: fadB (3-hydroxyacyl-CoA dehydrogenase and enoyl-CoA hydratase) | | | | |
| RB02 ΔfadB [yqeF+ fucO+] | 0.000 | 0.00 | 2.96 | 0.19 |
| RB02 ΔfadB [yqeF+ fadB+] | 0.157 | 0.16 | 5.86 | 0.52 |
| RB02 ΔfadB [yqeF+] | 0.000 | 0.00 | 1.84 | 0.11 |
| Reaction ④: ydiO (predicted acyl-CoA dehydrogenase) | | | | |
| RB02 ΔydiO [yqeF+ fucO+] | 0.038 | 0.04 | 3.14 | 0.18 |
| RB02 ΔydiO [yqeF+ ydiO+] | 0.163 | 0.16 | 5.94 | 0.57 |
| RB02 ΔydiO [yqeF+] | 0.018 | 0.02 | 1.66 | 0.13 |
| Reaction ⑤: fucO (L-1,2-propanediol oxidoreductase/n-butanol dehydrogenase) | | | | |
| RB02 ΔfucO [yqeF+] | 0.040 | 0.04 | 2.75 | 0.38 |
| RB02 ΔfucO [yqeF+ fucO+] | 0.151 | 0.11 | 5.64 | 0.51 |
| RB02 [yqeF+] | 0.088 | 0.35 | 4.00 | 0.68 |

[a]THL: thiolase; HBD: hydroxy-acyl-CoA dehydrogenase; CRT: crotonase; BDH: butanol dehydrogenase; n.d.: not detected.
[b]The genotype of strain RB02 is as follows: fadR atoC(c) crp* ΔarcA ΔptaΔadhEΔfrdA.
[c]Experiments were run for 24 hours in shake flasks using glucose (1% w/v) minimal medium.
[d]Strains were grouped based on the relevance of their genotypes for specified reactions (see FIG. 1a).

TABLE 2

Cell growth, glucose utilization, product synthesis, and carbon recovery for wild-type and engineered strains grown on glucose minimal medium Table 2A. n-butanol synthesis in wild-type and engineered E. coli strains

| | Concentration (g/L) | | | |
|---|---|---|---|---|
| Strain | Cells | Glucose utilized | Butanol | % C-recovery[b] |
| MG1655 | 0.85 | 7.33 | 0.00 | 88.77 |
| fadR atoC(c) | 0.71 | 5.16 | 0.00 | 85.78 |
| fadR atoC(c) ΔarcA Δcrp crp* (RB01) | 0.53 | 6.43 | 0.00 | 90.23 |
| RB01 ΔadhE ΔfrdA Δpta (RB02) | 0.29 | 1.76 | 0.00 | 94.09 |
| RB02 [yqhD+] | 0.49 | 4.27 | 0.11 | 91.70 |
| RB02 [fucO+] | 0.41 | 3.66 | 0.23 | 98.48 |
| RB02 [yqeF+] | 0.68 | 4.00 | 0.35 | 97.13 |
| RB02 [yqeF+ fucO+] | 0.72 | 10.19 | 1.85 | 86.05 |
| RB02 ΔyqhD [yqeF+ fucO+] | 0.49 | 7.89 | 1.90 | 84.15 |
| RB02 ΔyqhD ΔeutE [yqeF+ fucO+] | 0.66 | 7.66 | 2.15 | 93.54 |

Table 2B. Synthesis of higher chain (C > 4) n-alcohols by derivatives of strain RB03 (RB02 ΔyqhD ΔfucO)

| | Concentration (g/L) | | | | | |
|---|---|---|---|---|---|---|
| Strain | Cells | Glucose utilized | n-C6—OH | n-C8—OH | n-C10—OH | % C-recovery[b] |
| RB03 ΔfadD [fadBA+] | 0.71 | 5.27 | 0.000 | 0.000 | 0.000 | 90.38 |
| RB03 [fadBA+ yiaY+] | 0.87 | 7.19 | 0.081 | 0.035 | 0.130 | 72.71 |
| RB03 ΔfadD [fadBA+ yiaY+] | 0.73 | 5.06 | 0.170 | 0.080 | 0.170 | 91.97 |
| RB03 [fadBA+ eutG+] | 0.73 | 4.68 | 0.170 | 0.040 | 0.000 | 97.50 |
| RB03 ΔfadD [fadBA+ eutG+] | 0.52 | 4.00 | 0.170 | 0.070 | 0.010 | 90.36 |
| RB03 [fadBA+ betA+] | 0.70 | 4.06 | 0.180 | 0.000 | 0.000 | 90.27 |

TABLE 2-continued

Cell growth, glucose utilization, product synthesis, and carbon recovery for wild-type and engineered strains grown on glucose minimal medium

| | | | | | | |
|---|---|---|---|---|---|---|
| RB03 ΔfadD [fadBA+ betA+] | 0.72 | 3.98 | 0.210 | 0.100 | 0.020 | 91.16 |

Table 2C. Synthesis of long-chain (C > 10) saturated fatty acids by RB03 derivatives

| | | Concentration (g/L) | | | | | | |
|---|---|---|---|---|---|---|---|---|
| Strain | Cells | Glucose utilized | C10:0 | C12:0 | C14:0 | C16:0 | C18:0 | % C-recovery[b] |
| RB03 ΔfadD [fadBA+] | 1.02 | 6.13 | 0.000 | 0.000 | 0.000 | 0.000 | 0.000 | 97.28 |
| RB03 ΔfadD [fadBA+ fadM+] | 0.72 | 3.07 | 0.000 | 0.000 | 0.000 | 0.700 | 0.180 | 98.14 |
| RB03 ΔfadD [fadBA+ yciA+] | 0.53 | 2.87 | 0.050 | 0.000 | 0.080 | 0.450 | 0.100 | 91.94 |

[a]Data represent averages from three samples taken from shake flask cultures grown on 2% (w/v) glucose minimal medium for: A. 24 h, B. 48 h, and C. 72 h.
[b]Carbon recovery was calculated by multiplying the "moles of product per mole of glucose" times the number of carbon atoms in the molecule.

TABLE 3

Strains used in this study

| Strains | Description/Genotype | Source |
|---|---|---|
| MG1655 | F- λ- ilvG- rfb-50 rph-1 | Cronon |
| fadR atoC(c) | MG1655 fadR atoC(con) | Dellomonoco |
| RB01 | MG1655 fadR atoC(con) ΔarcA Δcrp::crp* | This study |
| RB02 | MG1655 fadR atoC(con) ΔarcA Δcrp::crp* ΔadhE Δpta ΔfrdA | This study |
| RB02 ΔyqhD | MG1655 fadR atoC(con) ΔarcA Δcrp::crp* ΔadhE Δpta ΔfrdA ΔyqhD | This study |
| RB02 ΔeutE ΔyqhD | MG1655 fadR atoC(con) ΔarcA Δcrp::crp* ΔadhE Δpta ΔfrdA ΔeutE ΔyqhD | This study |
| RB02 ΔyqeF | MG1655 fadR atoC(con) ΔarcA Δcrp::crp* ΔadhE Δpta ΔfrdA ΔyqeF | This study |
| RB02 ΔfadB | MG1655 fadR atoC(con) ΔarcA Δcrp::crp* ΔadhE Δpta ΔfrdA ΔfadB | This study |
| RB02 ΔydiO | MG1655 fadR atoC(con) ΔarcA Δcrp::crp* ΔadhE Δpta ΔfrdA ΔydiO | This study |
| RB02 ΔfucO | MG1655 fadR atoC(con) ΔarcA Δcrp::crp* ΔadhE Δpta ΔfrdA ΔfucO | This study |
| RB03 | MG1655 fadR atoC(con) ΔarcA Δcrp::crp* ΔadhE Δpta ΔfrdA ΔfucO ΔyqhD | This study |
| RB03 ΔfadD | MG1655 fadR atoC(con) ΔarcA Δcrp::crp* ΔadhE Δpta ΔfrdA ΔfucO ΔyqhD ΔfadD | This study |

TABLE 4

Plasmids used in this study

| Plasmid | Description/Genotype | Source |
|---|---|---|
| pTrcHis2A | pTrcHis2A (pBR322-derived), oriR pMB1, lacI$^q$, bla | Invitrogen (Carlsbad, CA) |
| pTH fadBA | E. coli fadBA genes under trc promoter and lacI$^q$ control in pTrcHis2A | This study |
| pTH yqeF | E. coli yqeF gene under trc promoter and lacI$^q$ control in pTrcHis2A | This study |
| pZS blank | oriR pSC101*, tetR, cat, contains $P_{LtetO-1}$ | Yazdani |
| pZS atoB | E. coli atoB gene under control of $P_{LtetO-1}$(tetR, oriR SC101*, cat) | This study |
| pZS betA | E. coli betA gene under control of $P_{LtetO-1}$(tetR, oriR SC101*, cat) | This study |
| pZS eutG | E. coli eutG gene under control of $P_{LtetO-1}$(tetR, oriR SC101*, cat) | This study |
| pZS fadB | E. coli fadB gene under control of $P_{LtetO-1}$(tetR, oriR SC101*, cat) | This study |
| pZS fadM | E. coli fadM gene under control of $P_{LtetO-1}$(tetR, oriR SC101*, cat) | This study |
| pZS fucO | E. coli fucO gene under control of $P_{LtetO-1}$(tetR, oriR SC101*, cat) | This study |
| pZS yciA | E. coli yciA gene under control of $P_{LtetO-1}$(tetR, oriR SC101*, cat) | This study |

TABLE 4-continued

Plasmids used in this study

| Plasmid | Description/Genotype | Source |
|---|---|---|
| pZS ydiO | E. coli ydiO gene under control of $P_{LtetO-1}$(tetR, oriR SC101*, cat) | This study |
| pZS yiaY | E. coli yiaY gene under control of $P_{LtetO-1}$(tetR, oriR SC101*, cat) | This study |
| pZS yqhD | E. coli yqhD gene under control of $P_{LtetO-1}$(tetR, oriR SC101*, cat) | This study |

TABLE 5

Comparison of crp, fadR, and atoSC loci of engineered strain RB02 (fadR atoC(c) ΔarcA Δcrp::crp* ΔadhE Δpta ΔfrdA) and wild-type MG1655.

| Gene locus | Accession # for RB02 sequence | Mutations/insertions in RB02 sequence | Comments |
|---|---|---|---|
| crp | BankIt1445305 Seq1 JF781281 | I113L, T128I, A145T | Mutations collectively reduce dependence on cAMP for activation of catabolic genes by CRP, as previously described[12, 45]. |
| fadR | BankIt1446148 Seq1 JF793627 | IS5 insertion between bp 395-396 of fadR gene | Inactivation of fadR by IS5 insertion, which would preclude synthesis of C-terminal half of FadR and hence DNA binding. Characteristic phenotype of fadR inactivation previously confirmed in strain fadR atoC(c)[10]. |
| atoSC | BankIt1445920 Seq1 JF793626 | I129S | atoC transduced from LS5218 (constitutive atoC expression[46]). Characteristic phenotype of constitutive expression of ato operon confirmed in strain fadR atoC(c)[10]. |

TABLE 6

Cell growth, glucose utilization, product synthesis, and carbon recovery for wild-type and engineered strains grown on glucose minimal medium[a]

Table 6A. Synthesis of n-butanol in wild-type and engineered E. coli strains

| | Concentration[c] (g/L) | | | |
|---|---|---|---|---|
| Strain[b] | Cells | Glucose utilized | Butanol | % C-recovery[d] |
| MG1655 | 0.85 | 7.33 | ND | 88.77 |
| fadR atoC(c) | 0.71 | 5.16 | ND | 85.78 |
| RB01 (fadR atoC(c) ΔarcA crp*) | 0.53 | 6.43 | ND | 90.23 |
| RB02 (RB01 ΔadhE ΔfrdA Δpta) | 0.29 | 1.76 | ND | 94.09 |
| RB02 [yqhD+] | 0.49 | 4.27 | 0.11 | 91.70 |
| RB02 [fucO+] | 0.41 | 3.66 | 0.23 | 98.48 |
| RB02 [yqeF+] | 0.68 | 4.00 | 0.35 | 97.13 |
| RB02 [yqeF+ fucO+] | 0.72 | 10.19 | 1.85 | 86.05 |
| MG1655 [yqeF+ fucO+] | 0.94 | 7.95 | ND | 91.15 |
| RB02 ΔyqhD [yqeF+ fucO+] | 0.49 | 7.89 | 1.90 | 84.15 |
| RB02 ΔyqhD ΔeutE [yqeF+ fucO+] | 0.66 | 7.66 | 2.15 | 93.54 |

Table 6B. Synthesis of 4-C carboxylic acids by derivatives of strain RB02

| | Concentration[c] (g/L) | | | | |
|---|---|---|---|---|---|
| Strain[b] | Cells | Glucose utilized | β-keto-C4:0 | β-hydroxy-C4:0 | trans-2-butenoic acid | % C-recovery[d] |
| RB02 | 0.29 | 1.76 | ND | ND | ND | 94.09 |
| RB02 [tesA+] | 0.62 | 4.25 | ND | 0.032 | 0.010 | 95.30 |
| RB02 [tesB+] | 0.57 | 4.30 | 0.024 | ND | ND | 89.88 |
| RB02 [yqeF+ tesA+] | 0.56 | 4.95 | ND | 0.045 | 0.012 | 91.08 |
| RB02 ΔydiO [yqeF+ tesA+] | 0.42 | 3.34 | ND | 0.140 | 0.171 | 89.23 |

TABLE 6-continued

Cell growth, glucose utilization, product synthesis, and carbon recovery for wild-type and engineered strains grown on glucose minimal medium[a]

| | | | | | | |
|---|---|---|---|---|---|---|
| RB03 [yqeF+ tesB+] | 0.65 | 5.16 | 0.110 | ND | ND | 97.17 |
| RB03 ΔfadB [yqeF+ tesB+] | 0.62 | 5.03 | 0.450 | ND | ND | 95.53 |

Table 6C. Synthesis of long-chain (C > 10) saturated fatty acids by RB03 (RB02 ΔyqhD ΔfucO ΔfadD) derivatives

| | | Concentration[c] (g/L) | | | | | | | | |
|---|---|---|---|---|---|---|---|---|---|---|
| | | Extracellular FFAs (Free Fatty Acids) | | | | | | | | |
| Strain[b] | Cells | Glucose utilized | C10:0 | C12:0 | C14:0 | C16:0 | C18:0 | Total FFAs[e] | TotalFFAs/CDW | % C-recovery[d] |
| MG1655 | 1.29 | 12.88 | ND | ND | ND | ND | ND | ND | / | 93.05 |
| RB03 | 0.63 | 4.30 | ND | ND | ND | ND | ND | ND | / | 90.64 |
| RB03 [fadBA+] | 0.51 | 2.24 | ND | ND | ND | ND | ND | 0.090 | 0.175 | 91.55 |
| RB03 [fadBA+ tesA+] | 0.56 | 5.82 | ND | ND | 0.110 | ND | ND | —[f] | — | 92.02 |
| RB03 [fadBA+ tesB+] | 0.62 | 5.16 | 0.120 | ND | ND | ND | ND | —[f] | — | 94.78 |
| RB03 [fadBA+ yciA+] | 0.53 | 2.87 | 0.050 | ND | 0.080 | 0.450 | 0.100 | —[f] | — | 91.94 |
| RB03 [fadBA+ fadM+] | 0.72 | 3.07 | ND | ND | ND | 0.700 | 0.180 | —[f] | — | 98.14 |
| RB03 [fadM+][g] | 0.55 | 3.30 | ND | ND | 0.020 | 0.150 | 0.080 | 0.435 | 0.790 | 92.86 |
| RB03 [fadBA.fadM+] | 0.67 | 5.91 | ND | ND | ND | 0.740 | 0.500 | 1.370 | 2.035 | 97.19 |
| MG1655 ΔadhE Δpta ΔfrdA ΔfadD | 0.38 | 5.04 | ND | ND | ND | ND | ND | ND | / | 86.44 |
| MG1655 ΔadhE Δpta ΔfrdA ΔfadD [fadM+] | 0.76 | 5.07 | ND | ND | ND | ND | ND | 0.070 | 0.092 | 94.15 |
| MG1655 ΔadhE Δpta ΔfrdA ΔfadD [fadM+][g] | 0.94 | 5.23 | ND | ND | ND | ND | ND | 0.261 | 0.279 | 96.17 |

Table 6D. Synthesis of higher chain (C > 4) n-alcohols by derivatives of strain RB03 (RB02 ΔyqhD ΔfucO ΔfadD)

| | Concentration[c] (g/L) | | | | | |
|---|---|---|---|---|---|---|
| Strain[b] | Cells | Glucose utilized | n-C6—OH | n-C8—OH | n-C10—OH | % C-recovery[a] |
| MG1655 ΔadhE Δpta ΔfrdA ΔfadD [betA+] | 0.65 | 4.16 | ND | ND | ND | 91.54 |
| RB03 [fadBA+] | 0.71 | 5.27 | ND | ND | ND | 90.38 |
| RB03 [fadBA+ yiaY+] | 0.73 | 5.06 | 0.170 | 0.080 | 0.170 | 91.97 |
| RB03 [fadBA+ eutG+] | 0.52 | 4.00 | 0.170 | 0.070 | 0.010 | 90.36 |
| RB03 [fadBA+ betA+] | 0.72 | 3.98 | 0.210 | 0.100 | 0.020 | 91.16 |

[a]Data represent averages for three samples taken from shake flask cultures grown on 2% (w/v) glucose minimal medium. A. cultures were grown at 30° C. for 24 hours; B., C., D. cultures were grown at 37° C. for 48 hours.
[b]All genotypes are shown in Table 4.
[c]ND, not detecTable. Minimum detection levels are: butanol, 5.84 mg l$^{-1}$; β-keto-C4:0, 4.09 mg l$^{-1}$; β-hydroxy-C4:0, 3.03 mg l$^{-1}$ trans-2-butenoic acid, 9.40 mg l$^{-1}$; C10:0, 21.76 mg l$^{-1}$; C12:0, 20.45 mg l$^{-1}$; C14:0, 27.12 mg l$^{-1}$; C16:0, 20.17 mg l$^{-1}$; C18:0, 16.42 mg l$^{-1}$; n-C6—OH, 24.21 mg l$^{-1}$; n-C8—OH, 26.41 mg l$^{-1}$; n-C10—OH, 21.23 mg l$^{-1}$.
[d]Carbon recovery was calculated as the ratio of total moles of carbon in products per moles of carbon in total glucose consumed and expressed on percentage basis.
[e]FFAs, Free Fatty Acids
[f]Values not measured
[g]fadM was overexpressed from medium-copy vector pTrcHis2A (Invitrogen, Carlsbad, CA).

TABLE 7

In silico identification of *E. coli* surrogates for higher-chain (C ≥ 4) aldehyde-forming acyl-CoA reductases and aldehyde/alcohol dehydrogenases (reaction in FIG. 1). Genes shown in bold were tested in this study.

| Organism | Source of gene sequences used to identify *E. coli* surrogates | | | | Surrogates identified via I-TASSER[47] | | | | Surrogates identified via protein BLAST[48] | | | |
|---|---|---|---|---|---|---|---|---|---|---|---|---|
| | Accession # | Gene | EC # | FUNCTION | EC # | TM-Score[a] | EC-Score[b] | Gene | Gene | E-value[c] | Identity | Similarity |
| *Identification of E. coli surrogates for higher-chain (C ≥ 4) fatty aldehyde-forming acyl-CoA reductase* | | | | | | | | | | | | |
| *Clostridium saccharobutylicum*[49] | P13604 | adh1 | 1.1.1.— | NADH-dependent butyraldehyde/butanol dehydrogenase | 1.1.1.77 | 0.9404 | 2.2424 | fucO | adhE | 2.0E-91 | 42% | 62% |
| | | | | | 1.1.1.— | 0.8679 | 1.8069 | yiaY adhE adhP frmA | fucO yiaY eutG yqhD | 5.0E-66 2.0E-65 4.0E-61 6.0E-28 | 35% 37% 35% 25% | 58% 56% 54% 46% |
| | | | | | 1.1.1.6 | 0.7979 | 1.4449 | gldA | | | | |
| *Pseudomonas* sp. strain CF600[50] | Q52060 | dmpF | 1.2.1.10 | Acetaldehyde dehydrogenase | 1.2.1.12 | 0.7439 | 1.3969 | gapA | mhpF | 6.0E-146 | 79% | 92% |
| *Acinetobacter* sp. Strain M-1[51] | Q8RR58 | acrM | 1.2.1.50 | Acyl coenzyme A reductase | | | <1.1[b] | | ucpA | 5.0E-20 | 31% | 49% |
| | | | | | | | | | ybbO ydfG idnO | 4.0E-19 6.0E-18 9.0E-18 | 30% 27% 29% | 50% 47% 49% |
| *Acinetobacter calcoaceticus*[52] | P94129 | acrI | 1.2.1.n2 | Fatty acyl-CoA reductase | | | <1.1[b] | | fab5G fabG idnO ydfG ybbO ucpA | 9.0E-17 2.0E-18 3.0E-17 1.0E-16 1.0E-16 2.0E-16 | 31% 31% 29% 27% 28% 31% | 51% 53% 48% 47% 44% 52% |
| *Identification of E. coli surrogates for higher-chain (C ≥ 4) aldehyde/alcohol dehydrogenases* | | | | | | | | | | | | |
| *Geobacillus thermodenitrificans*[51] | A4IP64 | GTNG_1754 | 1.1.1.— | Alcohol Dehydrogenase | 1.1.1.202 | 0.9565 | 2.5069 | yqhD | eutG | 3.0E-57 | 39% | 57% |
| | | | | | 1.1.1.77 1.1.1.— | 0.9312 0.8512 | 2.1532 1.9177 | fucO yiaY adhE adhP | yiaY fucO adhE yqhD | 3.0E-54 2.0E-52 3.0E-43 1.0E-18 | 33% 34% 34% 28% | 52% 53% 52% 46% |
| | | | | | 1.1.1.6 | 0.7715 | 1.5259 | frmA gldA | | | | |

TABLE 7-continued

In silico identification of *E. coli* surrogates for higher-chain (C ≥ 4) aldehyde-forming acyl-CoA reductases and aldehyde/alcohol dehydrogenases (reaction in FIG. 1). Genes shown in bold were tested in this study.

| Organism | Source of gene sequences used to identify *E. coli* surrogates | | | | Surrogates identified via I-TASSER[47] | | | | Surrogates identified via protein BLAST[48] | | | |
|---|---|---|---|---|---|---|---|---|---|---|---|---|
| | Accession # | Gene | EC # | FUNCTION | EC # | TM-Score[a] | EC-Score[b] | Gene[b] | EC # | Gene | E-value[c] | Identity | Similarity |
| *Pseudomonas oleovorans*[54] | Q00593 | alkJ | 1.1.99.— | Alcohol Dehydrogenase | | | | | 1.1.99.1 | betA | 2.0E-104 | 40% | 59% |
| *Thermococcus* sp. ES1[55] | C1IWT4 | adh | 1.1.1.1 | Iron alcohol dehydrogenase | 1.1.1.202 | 0.9301 | 2.2696 | yqhD | 1.1.1.1 | yiaY | 7.0E-40 | 33% | 50% |
| | | | | | 1.1.1.77 | 0.9041 | 1.9642 | fucO | 1.1.1.1 | yqhD | 4.0E-30 | 30% | 46% |
| | | | | | 1.1.1.1. | 0.8352 | 1.8286 | yiaY | 1.1.—.— | eutG | 3.0E-27 | 30% | 46% |
| | | | | | | | | adhE | 1.1.1.1. | adhE | 9.0E-27 | 29% | 48% |
| | | | | | | | | adhP | | | | | |
| | | | | | | | | frmA | | | | | |
| *Thermococcus hydrothermalis*[56] | Y14015 | | 1.1.1.— | Alcohol Dehydrogenase | 1.1.1.6 | 0.7800 | 1.3793 | gldA | 1.1.1.1 | yiaY | 4.0E-37 | 31% | 48% |
| | | | | | | | | | 1.1.—.— | eutG | 2.0E-34 | 31% | 47% |
| | | | | | | | | | 1.1.1.1. | adhE | 1.0E-30 | 30% | 50% |
| | | | | | | | | | 1.1.1.77 | fucO | 4.0E-30 | 30% | 45% |
| | | | | | | | | | 1.1.1.1 | yqhD | 5.0E-19 | 30% | 44% |
| *Sulfolobus tokodaii*[57] | Q976Y8 | ST0053 | 1.1.1.— | Hypothetical alcohol dehydrogenase | 1.1.1.1. | 0.9655 | 1.8286 | yiaY | 1.1.1.1. | adhP | 4.0E-33 | 31% | 50% |
| | | | | | | | | adhE | 1.—.—.— | ydjJ | 8.0E-26 | 30% | 50% |
| | | | | | | | | adhP | 1.—.—.— | yphC | 2.0E-21 | 31% | 47% |
| | | | | | | | | frmA | 1.—.—.— | yahK | 2.0E-21 | 29% | 45% |
| | | | | | | | | | 1.1.1.— | rspB | 6.0E-21 | 29% | 49% |
| | | | | | | | | | 1.1.1.103 | tdH | 9.0E-20 | 27% | 47% |
| | | | | | | | | | 1.—.—.— | yjjN | 3.0E-19 | 26% | 45% |
| | | | | | | | | | 1.1.—.— | gatD | 1.0E-18 | 28% | 44% |

[a]The Template Modeling-score (TM-score) is defined to assess the topological similarity of protein structure pairs. Its value ranges between 0 and 1, and a higher score indicates better structural match. Statistically, a TM-score <0.17 means a randomly selected protein pair with the gapless alignment taken from PDB[47].
[b]An EC-score >1.1 is a good indicator of the functional similarity between the query and the identified enzyme analogs[47].
[c]The BLAST E-value measures the statistical significance threshold for reporting protein sequence matches against the organism genome database; the default threshold value is 1E-5, in which 1E-5 matches would be expected to occur by chance, according to the stochastic model of Karlin and Altschul (ncbi.nlm.nih.gov/BLAST/tutorial/).

| Product | Engineered Host | Titer (g/L)/ Yield (% w/w)[a] | Fermentation Time (hr) | Carbon Source | Medium/ Cultivation | Reference |
|---|---|---|---|---|---|---|
| | Table 8A Summary of organisms that have been engineered to produce higher-chain (C ≥ 4) linear n-alcohols and long-chain (C ≥ 10) fatty acids  Higher-chain (C ≥ 4) linear n-alcohols | | | | | |
| n-butanol (C4) | E. coli | 0.55/2.8 | 24 | Glycerol | Rich/Batch | 35 |
| | E. coli | 0.82/3.3 | 100 | Glucose | Rich/Batch | 7,8 |
| | E. coli | 1.2/6.1 | 60 | Glucose | Rich-MM/HCD[b] | 58 |
| | E. coli | 0.58/11.6 | 48 | Glycerol | Rich/Batch | 59 |
| | S. cerevisiae | 0.002/0.0001 | 72 | Galactose | Rich/Batch | 60 |
| | B. subtilis | 0.024/0.48 | 72 | Glycerol | Rich/Batch | 59 |
| | P. putida | 0.120/2.4 | 72 | Glycerol | Rich/Batch | 59 |
| | L. lactis | 0.028/— | — | Glucose | Rich/Batch | 61 |
| | L. buchneri | 0.066/— | — | Glucose | Rich/Batch | 61 |
| | L. brevis | 0.3/1.5 | 60 | Glucose | Rich/Batch | 41 |
| | E. coli | 2.05/13.4 | 96 | Palmitic Acid | MM/Fed-Batch | 10 |
| | E. coli | 4.65/28 | 72 | Glucose | Rich/Batch | 9 |
| | E. coli | 14.5/32.8 | 36 | Glucose | MM/Batch | This work |
| n-hexanol (C6) | E. coli | 0.04/0.2 | 40 | Glucose | Rich/Batch | 29 |
| Fatty alcohols (Distribution of C10, C12, C14, and C16) | E. coli | 0.06/0.3 | — | Glucose | MM/Batch | 2 |
| Higher-chain n-alcohols (C6 to C10) | E. coli | 0.42/8.3 | 48 | Glucose | MM/Batch | This work |
| | Table 8B Summary of organisms that have been engineered to produce higher-chain (C ≥ 4) linear n-alcohols and long-chain (C ≥ 10) fatty acids  Long-chain (C ≥ 10) fatty acids | | | | | |
| Fatty Acids (Predominantly C14) | E. coli | 1.2/6 | — | Glucose | MM/Batch | 2[c] |
| Fatty Acids (Wide Distribution) | E. coli | 2.5/— | 22 | Glycerol | MM/Fed-Batch/HCD | 62[c] |
| Fatty Acids (Predominantly C12) | E. coli | 0.81/16 | 29 | Glycerol | Rich Batch | 4[c] |
| Fatty Acids (Predominantly C16, C18) | E. coli | 6.6/28 | 60 | Glucose | MM/Batch | This work |

[a] For products with carbon length distributions, titer represents the sum of products of all chain length produced. Yield assumes all the carbon source was consumed when carbon source consumption data not given in reference.
[b] Two-phase, high cell density (HCD) culture grown first in rich medium and then incubated in minimal medium (MM).
[c] Titers reported refer to total (i.e. sum of intracellular and extracellular) free fatty acids.

TABLE 9

Homology analysis and functional annotation of E. coli ydi genes

| Current annotation[a] | | Sequence-based homologues identified via protein BLAST[46] | | | | | Functional homologues identified via I-TASSER[47] | | |
|---|---|---|---|---|---|---|---|---|---|
| Gene name | Function | Gene | Function | E-value[a] | Coverage | Similarity | Function | TM-Score[c] | EC-Score[a] |
| ydiO | Predicted acyl-CoA dehydrogenase | caiA | Crotonobetainyl-CoA reductase | 1.0E−102 | 99% | 65% | Butyryl-CoA dehydrogenase | 0.9584 | 2.2964 |
| | | aidB | Isovaleryl-CoA dehydrogenase | 2.0E−14 | 64% | 47% | Acyl-CoA dehydrogenase | 0.9618 | 2.1730 |
| | | fadE | Acyl-CoA dehydrogenase | 0.001 | 81% | 37% | | | |
| ydiQ | Putative electron transfer flavoprotein subunit | fixA | probable flavoprotein subunit required for anaerobic carnitine metabolism | 3.0E−68 | 99% | 71% | Adenosine kinase | | <1.1 |
| ydiR | Putative electron transfer flavoprotein subunit | fixB | probable flavoprotein subunit required for anaerobic carnitine metabolism | 6.0E−75 | 100% | 64% | | | |
| ydiS | Predicted oxidoreductase with FAD/NAD(P)-binding domain | fixC | flavoprotein (electron transport) | 5.0E−152 | 100% | 78% | Electron-transferring-flavoprotein dehydrogenase | 0.9404 | 1.8378 |
| | | ygcN | predicted oxidoreductase with FAD/NAD(P)-binding domain | 9.0E−93 | 99% | 62% | | | |
| ydiT | Ferredoxin-like protein | fixX | putative ferredoxin possibly involved in anaerobic carnitine metabolism | 3.0E−33 | 96% | 62% | Electron-transferring-flavoprotein dehydrogenase | 0.9006 | 1.5362 |

TABLE 9-continued

Homology analysis and functional annotation of *E. coli* ydi genes

| Current annotation[a] | | Sequence-based homologues identified via protein BLAST[46] | | | | Functional homologues identified via I-TASSER[47] | |
|---|---|---|---|---|---|---|---|
| Gene name | Function | Gene | Function | E-value[a] | Coverage | Similarity | Function | TM-Score[c] | EC-Score[a] |
| | | ygcO | predicted 4Fe—4S cluster-containing protein | 1.0E−18 | 89% | 62% | | | |

[a]As annotated in Ecocyc[63]. Also reported by Campbell, J. W. and coworkers[64].
[b]The BLAST E-value measures the statistical significance threshold for reporting protein sequence matches against the organism genome database; the default threshold value is 1E−5, in which 1E−5 matches would be expected to occur by chance, according to the stochastic model of Karlin and Altschul ncbi.nlm.nih.gov/BLAST/tutorial/).
[c]The Template Modeling-score (TM-score) is defined to assess the topological similarity of protein structure pairs. Its value ranges between 0 and 1, and a higher score indicates better structural match. Statistically, a TM-score <0.17 means a randomly selected protein pair with the gapless alignment taken from PDB[47].
[d]An EC-score >1.1 is a good indicator of the functional similarity between the query and the identified enzyme analogs[47].

TABLE 10

Thermodynamic analysis of the engineered reversal of the β-oxidation cycle

| Reaction number and enzyme name (gene) | Standard $\Delta G_r$ (Min $\Delta G_r$, Max $\Delta G_r$) [kcal/mol][a] |
|---|---|
| ① Thiolase (yqeF, fadA) 2 Acetyl-CoA → Acetoacetyl-CoA + CoA-SH | 7.1 (−1.9, 16.1) |
| ② Hydroxyacyl-CoA dehydrogenase (fadB) Acetoacetyl-CoA + NADH + H⁺ → 3-hydroxybutyryl-CoA + NAD⁺ | −3.7 (−12.7, 5.3) |
| ③ Enoyl-CoA hydratase (fadB) 3-hydroxybutyryl-CoA → Crotonyl-CoA + H$_2$O | 2.1 (−2.4, 6.6) |
| ④ Acyl-CoA dehydrogenase (coupled to ubiquinone, fadE)[b] Crotonyl-CoA + UQH$_2$ → Butyryl-CoA + UQ | 5.7 (−3.3, 14.7) |
| ④ Enoyl-CoA reductase (coupled to ferredoxin, ydiO-ydiQRST)[b] Crotonyl-CoA + Fd$^2$ → Butyryl-CoA + Fd | −16.5 (−25.5, −7.5) |
| Operation of β-oxidation reversal coupled to ubiquinone | 11.2 |
| Operation of β-oxidation reversal coupled to ferredoxin | −11.0 |

[a] Standard ΔG of formation values estimated using the group contribution method[65] and used to calculate the standard ΔG of reaction[66]. Minimum and maximum ΔG$_r$ values calculated assuming standard conditions (298.15 K, pH 7) with minimum and maximum metabolite concentrations set to 0.00001M and 0.02M, respectively[66]. Listed ΔG$_r$ values are in good agreement with experimentally measured/calculated ΔG$_r$ values[67, 68].
[b]Calculation of ΔG$_r$ for enoyl-CoA reductase used standard reduction potentials from Thauer et al[67].

The following references are incorporated herein by reference in their entirety:

Atsumi, S. et al. Metabolic engineering of *Escherichia coli* for 1-butanol production. Metab. Eng. 10, 305-311 (2008).

Atsumi, S., et al. Non-fermentative pathways for synthesis of branched-chain higher alcohols as biofuels. Nature 451, 86-89 (2008).

Bond-Watts, B. B., et al., Enzyme mechanism as a kinetic control element for designing synthetic biofuel pathways. Nat. Chem. Biol. 7, 222-227 (2011).

Clark, D. P. & Cronan, J. E. in *Escherichia coli* and *Salmonella*: cellular and molecular biology (ed. Neidhart, F. C.) Ch. 3.4.4, 343-357 (American Society for Microbiology, Washington D.C., 2005).

Cronan, J. E. & Thomas, J. Bacterial fatty acid synthesis and its relationships with polyketide synthetic pathways. Methods Enzymol. 459, 395-433 (2009).

Dellomonaco, C., Rivera, C., Campbell, P. & Gonzalez, R. Engineered respiro-fermentative metabolism for the production of biofuels and biochemicals from fatty acid-rich feedstocks. Appl. Environ. Microbiol. 76, 5067-5078 (2010).

Dellomonaco, C., Clomburg, J. M., Miller, E. N., and Gonzalez, R. Engineered reversal of the β-oxidation cycle for the synthesis of fuels and chemicals. Nature 476, 355-359 (2011).

Eppler, T. & Boos, W. Glycerol-3-phosphate-mediated repression of malT in *Escherichia coli* does not require metabolism, depends on enzyme IIA(Glc) and is mediated by cAMP levels. Mol. Microbiol. 33, 1221-1231 (1999).

Frias, et al., Purification and characterization of OleA from *Xanthomonas campestris* and demonstration of a non-decarboxylative Claisen condensation reaction. Journal of Biological Chemistry, 286:10930-10938 (2011).

Haapalainen, A. M., et al., The thiolase superfamily: condensing enzymes with diverse reaction specificities. Trends Biochem. Sci. 31, 64-71 (2006).

Handke, P., et al., Application and engineering of fatty acid biosynthesis in *Escherichia coli* for advanced fuels and chemicals. Metab. Eng. 13, 28-3 (2010).

Hoffmeister, M., et al., Mitochondrial trans-2-Enoyl-CoA Reductase of Wax Ester Fermentation from *Euglena gracilis* Defines a New Family of Enzymes Involved in Lipid Synthesis. Journal of Biological Chemistry, 280, 4329-4338 (2005).

Ishige T., et al., Wax Ester Production from n-Alkanes by *Acinetobacter* sp. Strain M-1: Ultrastructure of Cellular Inclusions and Role of Acyl Coenzyme A Reductase. Applied and Environmental Microbiology, 68, 1192-1195 (2002).

Kim, Y., et al., Construction of an *Escherichia coli* K-12 mutant for homoethanologenic fermentation of glucose or xylose without foreign genes. Applied and Environmental Microbiology, 73, 1766-1771 (2007).

Lalman, J. A. & Bagley, D. M. Extracting long-chain fatty acids from a fermentation medium. J. Am. Oil Chem. Soc. 81, 105-110 (2004).

Lennen, R. M., et al., A process for microbial hydrocarbon synthesis: Overproduction of fatty acids in *Escherichia coli* and catalytic conversion to alkanes. Biotechnol. Bioeng. 106, 193-202 (2010).

Neidhart, F. C., et al., Culture media for enterobacteria. Journal of Bacteriology 119, 736-747 (1974).

Poirier, Y., et al., Peroxisomal β-oxidation—A metabolic pathway with multiple functions. Biochim. Biophys. Acta 1763, 1413-1426 (2006).

Reiser, S, and Somerville, C. Isolation of mutants of *Acinetobacter calcoaceticus* deficient in wax ester synthesis and complementation of one mutation with a gene encoding a fatty acyl coenzyme A reductase. J. of Bacteriol., 179, 2969-2975 (1997).

Rotte, C., et al., Pyruvate:NADP+ oxidoreductase from the mitochondrion of *Euglena gracilis* and from the apicomplexan *Cryptosporidium parvum*: a biochemical relic linking pyruvate metabolism in mitochondriate and amitochondriate protists. *Molecular Biology and Evolution*, 18, 710-720 (2001).

Schirmer, A., et al., Microbial Biosynthesis of Alkanes. Science, 329, 559-562 (2010).

Schutte, H., et al., Purification and Properties of Formaldehyde Dehydrogenase and Formate Dehydrogenase from *Candida boidinii*. *European Journal of Biochemistry*, 62, 151-160 (1976).

Shen, C. R. & Liao, J. C. Metabolic engineering of *Escherichia coli* for 1-butanol and 1-propanol production via the keto-acid pathways. Metab. Eng. 10, 312-320 (2008).

Steen, E. J. et al. Microbial production of fatty-acid-derived fuels and chemicals from plant biomass. Nature 463, 559-562 (2010).

Sukovich, D. J., et al., Structure, function, and insights into the biosynthesis of a head-to-head hydrocarbon in *Shewanella oneidensis* strain MR-1. Applied and Environmental Microbiology, 76, 3842-3849 (2010a).

Sukovich, D. J., et al., Widespread head-to-head hydrocarbon biosynthesis in bacteria and role of OleA. Applied and Environmental Microbiology, 76, 3850-3862 (2010b).

Yazdani, S. S. & Gonzalez, R. Engineering *Escherichia coli* for the efficient conversion of glycerol to ethanol and co-products. Metab. Eng. 10, 340-351 (2008).

What is claimed is:

1. An engineered microorganism, wherein the microorganism is engineered to overexpress β-oxidation cycle enzymes and one or more termination enzymes as compared to a corresponding wild-type microorganism, wherein said β-oxidation cycle enzymes comprise:
   a) a thiolase catalyzing the conversion of ($C_n$)-acyl CoA to β-ketoacyl-CoA,
   b) a hydroxyacyl-CoA dehydrogenase catalyzing the conversion of β-ketoacyl-CoA to β-hydroxyacyl-CoA,
   c) an enoyl-CoA hydratase catalyzing the conversion of β-hydroxyacyl-CoA to trans-Δ2-Enoyl-CoA, and
   d) an acyl-CoA dehydrogenase or transenoyl-CoA reductase catalyzing the conversion of trans-Δ2-enoyl-CoA to ($C_{n+2}$)-acyl CoA,
   wherein said β-oxidation cycle runs in the reverse/biosynthetic direction, as recited in enzyme reactions a) through d),
   and
   wherein said one or more termination enzymes are selected from the group consisting of an alcohol-forming coenzyme-A thioester reductase; an aldehyde-forming CoA thioester reductase and an alcohol dehydrogenase; a thioesterase; an acyl-CoA:acetyl-CoA transferase; a phosphotransacylase and a carboxylate kinase; an aldehyde-forming CoA thioester reductase and an aldehyde decarbonylase; and OleA, OleB, OleC, and OleD.

2. An engineered microorganism comprising a genotype, wherein said genotype comprises fadR, atoC(c), ΔarcA, Δcrp, crp*.

3. The engineered microorganism of claim 2, wherein said genotype is selected from the group consisting of:
   a) fadR, atoC(c), ΔarcA, Δcrp, crp*, ΔadhE, ΔfrdA, Δpta, ΔldhA, ΔmgsA, [tesB+];
   b) fadR, atoC(c), ΔarcA, Δcrp, crp*, ΔadhE, ΔfrdA, Δpta, ΔldhA, ΔmgsA, [tesB+, yqeF+]; and
   c) fadR, atoC(c), ΔarcA, Δcrp, crp*, ΔadhE, ΔfrdA, Δpta, ΔldhA, ΔmgsA, ΔfadB, [tesB+, yqeF+].

4. The engineered microorganism of claim 2, wherein said genotype is selected from the group consisting of:
   a) fadR, atoC(c), ΔarcA, Δcrp, crp*, ΔadhE, ΔfrdA, Δpta, ΔldhA, ΔmgsA, [tesA+];
   b) fadR, atoC(c), ΔarcA, Δcrp, crp*, ΔadhE, ΔfrdA, Δpta, ΔldhA, ΔmgsA, [tesA+, yqeF+]; and
   c) fadR, atoC(c), ΔarcA, Δcrp, crp*, ΔadhE, ΔfrdA, Δpta, ΔldhA, ΔmgsA, ΔydiO, [tesB+, yqeF+].

5. The engineered microorganism of claim 2, wherein said genotype is selected from the group consisting of:
   a) fadR, atoC(c), ΔarcA, Δcrp, crp*, ΔadhE, ΔfrdA, Δpta, ΔyqhA, ΔfucO, ΔfadD, ΔydiO, [yqeF+, tesB+];
   b) fadR, atoC(c), ΔarcA, Δcrp, crp*, ΔadhE, ΔfrdA, Δpta, ΔyqhA, ΔfucO, ΔfadD, [fadBA+, fadM+]; and
   c) fadR, atoC(c), ΔarcA, Δcrp, crp, ΔadhE, ΔfrdA, Δpta, ΔyqhA, ΔfucO, ΔfadD, [fadBA+, yciA+].

6. The engineered microorganism of claim 2, wherein said genotype is selected from the group consisting of:
   a) fadR, atoC(c), ΔarcA, Δcrp, crp*, ΔadhE, ΔfrdA, Δpta, ΔyqhA, ΔfucO, ΔfadD, [yqeF+, acrM+, PCC7942_orf1593+];
   b) fadR, atoC(c), ΔarcA, Δcrp, crp*, ΔadhE, ΔfrdA, Δpta, ΔyqhA, ΔfucO, ΔfadD, [yqeF+, acrl+, PCC7942_orf1593+];
   c) fadR, atoC(c), ΔarcA, Δcrp, crp*, ΔadhE, ΔfrdA, Δpta, ΔyqhA, ΔfucO, ΔfadD, [yqeF+, oleABCD+];
   d) fadR, atoC(c), ΔarcA, Δcrp, crp*, ΔadhE, ΔfrdA, Δpta, ΔyqhA, ΔfucO, ΔfadD, [fadBA+, acrM+, PCC7942_orf1593+];
   e) fadR, atoC(c), ΔarcA, Δcrp, crp*, ΔadhE, ΔfrdA, Δpta, ΔyqhA, ΔfucO, ΔfadD, [fadBA+, acrl+, PCC7942_orf1593+]; and
   f) fadR, atoC(c), ΔarcA, Δcrp, crp*, ΔadhE, ΔfrdA, Δpta, ΔyqhA, ΔfucO, ΔfadD, [fadBA+, oleABCD+].

7. A method of making a product, said method comprising growing the engineered microorganism of claim 1 under microaerobic (<10% $O_2$) or anaerobic conditions in a glucose minimal medium supplemented with 0-100 μM $FeSO_4$ and 0-5 mM calcium pantothenate at a temperature of 30-40° C. for a time sufficient to allow production of a product and isolating said product, wherein said product is selected from the group consisting of trans Δ2 fatty alcohols, β-keto alcohols, 1-3 diols, β-hydroxy acids, carboxylic acids, and hydrocarbons.

* * * * *